(12) United States Patent
Catlett

(10) Patent No.: US 6,348,033 B1
(45) Date of Patent: Feb. 19, 2002

(54) MAGNETIC THERAPEUTIC PENILE BAND DEVICE

(76) Inventor: James A. Catlett, 2712 Ore Bank Rd., Pigeon Forge, TN (US) 37863

( * ) Notice: Subject to any disclaimer, the term of this patent is extended or adjusted under 35 U.S.C. 154(b) by 0 days.

(21) Appl. No.: 09/444,647

(22) Filed: Nov. 22, 1999

(51) Int. Cl.[7] .............................. A61N 1/00; A61N 2/00
(52) U.S. Cl. ............................................. 600/15; 600/9
(58) Field of Search .............................. 600/1.3, 9, 1.5, 600/38, 31; 604/9, 54

(56) References Cited

U.S. PATENT DOCUMENTS

| | | | | |
|---|---|---|---|---|
| 4,587,956 A | * | 5/1986 | Griffin et al. | 600/15 |
| 5,017,185 A | * | 5/1991 | Baermann | 600/15 |
| 5,782,743 A | * | 7/1998 | Russel | 600/9 |

* cited by examiner

Primary Examiner—Eric F. Winakur
(74) Attorney, Agent, or Firm—M. Alex Brown

(57) ABSTRACT

A self-adjusting magnetic therapeutic band device, assembly, system and method of use is disclosed for use on, or in interaction with, a living penile organ of a human or animal. The invention is provided with differentially elastic layers and like fabricated or elastic layerings in embodiments of the invention as part of a securement or band-like piece, for securement, pocketing, and various spacings between, positioned magnetic groupings and magnetic components of embodiments of the invention, utilizing their opposing and like magnetic polar charges, to position the invention in contact with, and adjustment to, the changing sizes of a flaccid or erectile penile organ. The invention also contemporaneously provides a therapeutic magnetic field to tissue and anatomy adjacent or proximate to a pre-selected installation site on a penile organ. The invention utilizes various coupling systems or assemblies for such installation, achieving snug, contact-friendly interaction with a penile organ, while providing snug self-adjustment of the invention's layered band-like piece to various perimeter and size changes of the organ.

24 Claims, 17 Drawing Sheets

MAGNETIC THERAPEUTIC PENILE BAND DEVICE

FIELD OF THE INVENTION

The present invention relates to a penile band and collar device, biasable and self-adjusting in construction, for use, without surgery, in interaction with a penile organ having initial and further perimeter dimensions, with regard to which the device supplies movement, and magnetic and therapeutic effect.

BACKGROUND INFORMATION

No references were found specifically relating to the present invention in this crowded art. One reference which has marginal relation to the invention, though substantially different in structure and function is the Atchley, U.S. Pat. No. 3,636,948. Other distinguishable prior art; related to structural fabrication, general magnetic application or penile erection enhancing devices; found in the process of a patent search include U.S. Patents to Baermann, U.S. Pat. No. 5,017,185; Griffin et al., U.S. Pat. No. 4,587,956; Sherman, U.S. Pat. No. 2,597,601; Nakayama, U.S. Pat. No. 3,921,620; Griffith et al., U.S. Pat. No. 4,757,804; Ardizzone, U.S. Pat. No. 5,871,438; Mooreville et al., U.S. Pat. No. 5,803,897; Russell et al., U.S. Pat. No. 5,683,383; Schwaninger, U.S. Pat. No. 5,453,079; Khouri, U.S. Pat. No. 5,662,583; Merrill et al., U.S. Pat. No. 5,125,890; Gottschalk, U.S. Pat. No. 5,085,209; Susic, U.S. Pat. No. 5,084,003; Fischell, U.S. Pat. No. 4,941,461; and Stubling et al., U.S. Pat. No. 1,006,415.

Additionally, the published literature, or commercial advertising, has made reference in recent years to the general health benefits of magnetic or biomagnetic treatments to compromised or diseased areas of the body, although no specific similar reference to the structural and functional elements and benefits of the present invention has been found.

Specifically, the Atchley '948 patent reference teaches a "Therapeutic Device," and more particularly a male genital device for affecting or enhancing erection of the human penis. This reference further, structurally, teaches a resilient strip for being tightly wrapped around the penis near the base thereof, or pubic bone. The Atchley strip is provided with many radially extending projections, utilized, within the teaching of this reference, to restrict the flow of blood from the penis to produce an erection of the organ. In contradistinction with the present invention, Atchley does not teach the functional or structural application of magnetic field charge; band construction to permit and adjust to changing dimensions of a penile organ, of lesser or greater magnitude, i.e., self-adjusting function; or diversity of positional location of installment on a penile organ; as the present invention does. The Atchley reference further teaches 'sole' employment of a physical force-effect, to restrict blood vessels such as the subcutaneous dorsal vein and the deep dorsal vein, within the penis; rather than the application of a therapeutic magnetic field, and contemporaneous, self-adjusting size and pressure in relation to the entire cross-sectional anatomy of the penis, with a diversity of pre-selectable installment areas therealong; as is the case with the present invention, and its utilization.

The Baermann '185 reference teaches a "Permanent Magnetic Arrangement For Therapeutic Purposes," having two rubber-type magnetic foil strips in which permanent magnet 'particles' are embedded in fine distribution in a thermoplastic binder layer. As taught, the magnetic foil strips in this reference are of identical tubular form for surrounding a portion of the body such as part of an arm or leg having a fractured bone. Each of the foil strips is axially separate from each other. Each of the two foil strips taught have a radially inner surface and a corresponding radially outer surface. One of the inner surfaces is formed as a north magnetic pole, the other as a south magnetic pole, with each of the outer surfaces being formed of an opposite polarity to its corresponding inner surface. Individual application of layers of such strips is intended to augment opposite charge positioning only perpendicularly to the longitudinal axis of its tubular forms; and such individual layering is taught for optimal use of the Baermann device. Thus, in distinction from the present invention, additional layers of a tubular device are wrapped around a limb or cast on a limb.

Additionally, Baermann does not teach a true self-adjusting device, in the manner of the present invention, changeable and size-responsive to the changing cross-section or dimensions physiologically brought about within an organ. Nor is there any reason suggested in the Baermann teaching 'why' this would be important, or why this would constitute part of the use, structure or function of its magnetic foils. Additionally, the Baermann teaching with respect to magnet type, positional placement and magnetic function, as well as magnet securement, is substantially different from those of the present invention. Further, there is no specific or adequate general teaching set forth as to how or why this device would be adoptable, at all, to the physiology and anatomy of a penile organ. More specifically the Baermann reference distinguishably teaches the intended therapeutic applications for conditions such as a fractured bone; and is intended for use, as taught, in a layered, bandage-like manner, hence its teaching to position one of its devices over-the-other, or over a plaster cast on a bone fracture.

Griffin '956 teaches a reversible magnetic therapeutic device and method of use, principally designed to address strained and sprained muscles, bruised tissues and stiff and arthritic joints in fore and hind limbs, or arms and legs of animals and humans. In its broadest teaching, this reference provides for a two-sided flexible wrapper piece; claiming alternatively and indefinitely to enclose a limb "in either of two sleeve-like optional configurations with one or the other side of the wrapper" (emphasis added) piece "engaging the" limb. It does teach the use of magnets with a north-south axes. However, the magnets are deployed "perpendicularly to the plane of the wrapper and with all the north poles on one side of the wrapper and all the south poles on the other side;" (claim 1, Griffin, col. 12). Additionally, Griffin teaches a "lamination" of two flexible sheets" having separate compartments for individual magnets. Griffin further discloses/claims specific methods of use for its wrapper, in substantial distinction to the present invention, in teaching its steps in substantial relation to a fore limb or hind limb, of: (1) exposing the limb, "substantially completely around the periphery thereof" to a "north pole magnetic flux directed radially therein" to obtain a reduction in pain; and, then: (2) exposing the limb completely around its periphery to a south pole magnetic flux directed radially therein to restore the limb to healthy condition.

To ostensibly attempt to achieve this, Griffin provides for another method of use having the steps of: (1) applying its "wrapper as a sleeve completely enclosing" the limb, with the north poles of the magnets on one side of the wrapper being turned inwardly, for sufficient time to obtain reduction in pain; and then: (2) "removing and reversing the wrapper and reapplying it as a sleeve completely enclosing" the limb, "with the south poles of the magnets turned inwardly," for a sufficient time to obtain improvement in the health condition of the limb. Griffin's many examples of treatment problems, for which its device and method of use are intended to address, specifically stress and emphasize strained or sprained muscles, bruised tissues and stiff or arthritic joints of horses and humans, distinguishing 'pain' from 'healthy condition' in its treatment modalities. No mention is made, nor use addressed, adopted or disclosed; for treating any pathology, disease or blood circulation problems of a penile organ, as is the case of the present invention.

Also, Griffin does not disclose a truly, dimensionally responsive, self-adjusting comfort fit band for soft tissue application; but, rather, tight wrapping around a limb to achieve a certain stationary magnetic alignment. Additionally, the Griffin reference teaches, only application, along the limb's periphery of 'one' polar magnetic charge; namely, north or south, depending on which inward side of Griffin's wrapper is installed against the limb as a sleeve. While the present invention sets up a number of positive and negative magnetic field charges which are flux-oriented, both perpendicular to the perimeter of its band and along its lengthwise, elliptical, circumferential or other perimeter configurations; and does so in both contracted and self-adjusted, extended positions, without reversal of sides or repositioning of the present invention once initially installed. Nor does Griffin employ multiple component magnets, in preferred embodiments, to achieve its magnetic flux, as the present invention to achieve its magnetic field.

The Sherman '601 reference simply teaches a "Fisherman's Hatband" designed to hold flies, or other similar fishing accoutrements. Sherman teaches an axial array of individually secured magnets positioned in no meaningful or disclosed pattern, to extend on either side of its securement stitching. No therapeutic purpose is disclosed or addressed as an object of this invention; and as disclosed, structurally, no such function or purpose is encompassed in the Sherman teaching. Additionally, the hatband of Sherman is only adjustable, in strictly a preselected manual manner, by virtue of a separate connected resilient strap (its element 24) and fastener (26), as illustrated in FIGS. 1 and 2 of the Sherman drawings. Sherman's magnetic purpose is the further attraction of metal fishing items to the hatband, on which they are positioned, in vast distinction to the magnetic and therapeutic objects of the present invention.

The Nakayama '620 reference teaches a "Magnetic Medical Treatment Device"; the Griffith '804 reference, a "Device For Electromagnetic Treatment Of Living tissue"; and the Ardizzone '438 reference, a "Flexible Magnetic Pad With Multi-directional Constantly Alternating Polarity Zones." Each of these references teach a device substantially distinguishable, structurally and functionally from the present invention; having different magnetic or electrical arrays, positioning or patterning, and lacking self-adjusting means and invention objects relating to the therapeutic treatment of blood circulation and tissue pathologies of a physiologically compromised penile organ. They also differ in their respective means of installment and ability to therapeutically and positionally respond to the changing dimensions or size of a penile organ, among other differences.

The balance of the prior art found is even less relevant, structurally and functionally, to the present invention.

None of the references found in the prior art specifically illustrate, disclose or claim the Magnetic Therapeutic Penile Band Device of the present invention. Nor is the present invention obvious in view of any of the prior art listed, or reasonable combination thereof. In addition, all of the relevant prior art, such as it exists, heretofore known, suffer from a number of disadvantages.

None of the prior art devices, or respectively related methods of use, address the problem of providing a self-adjusting device sensitive to changing proportions or dimensionality of a penile organ, while continuing to produce and exert an axial and periphery magnetic field charge based on interacting polarities, differential band flexibility and construction and magnetic pocketing means; throughout the organ's natural changes in size.

The prior art also suffers in it inability to provide a user-friendly, comfort fit and self-adjustable therapeutic device or instrument of simple construction, for treating difficulties or pathology in the blood vessels, nerves, erectile tissue and muscles adjacent and functional with respect to a penile organ.

Also, none of the prior art devices or methods provide the reasonable structural and functional ability to easily reposition a therapeutic penile band device at various locations on a penile organ to address anatomical and physiological problems, accordingly, more relevant thereto.

Additional limitations in the prior art include providing securement, support or pocketing of single or multi-component magnetic charges in an effective arrangement so as to both allow for self-adjustment to size change in a penile organ and provide positive and negative magnetic charge interaction directly along the periphery or perimeter of such an organs while providing a uniform, comfortable and therapeutic pressure against a penal organ, which is non-emasculating and not physiologically invasive or interrupting in its nature.

These and other disadvantages, structurally and functionally, of the prior art, will become apparent in reviewing the remainder of the present specification, claims and exemplar illustrations.

Accordingly, to solve the problems endemic in the prior art, it is an object of the present invention to provide a size-self-adjusting, magnetically therapeutic penile band device having a differentially flexible securing band and magnet pocketing assembly layer, providing size responsive adjustment to changing penile organ size, and a magnetic field along and adjacent to the penile organ to therapeutically improve circulation and blood flow in such an organ; inadequate blood flow and circulation being the prime reasons for impotence or erectile dysfunction.

It is a further object of the invention to utilize in a special and novel manner the benefits known to exist in magnetic field treatment in the area of penile organ tissue; and to provide a device, in this regard, which will sizably adjust to a flaccid penile organ and a penile organ which experiences tumescence (swelling of the organ), change in penile circumference or perimeter, or the onset of an erectile state; responding in size to dimensions to all of these dimensional changes in a penile organ, while remaining substantially consistent or uniform in the pressure exerted by the present invention on such an organ.

It is a further related object of the invention to facilitate the necessary size adaptations of it support band by a special and novel placement of selected magnets formed in groups or portions and aligned in adjacent opposite magnetic poles, such that when the magnets mounted on the device attract each other during a general flaccid state, folded portions take up part of the perimeter of the invention's support band to fit snugly and comfortably to the penile organ, and when the magnetic groupings or portions are forced apart by the pressure of an enlarging penile organ, the folded portions are released to allow the available perimeter length of the invention's support band to comfortably adjust to the increased size of the penile organ without bringing to bear any substantial additional pressure on such an organ.

It is yet a further object of the invention to employ selected construction materials which better facilitate the invention's ability to be more responsive to its magnetic components, to affect the novel size adaptations in response to the given perimeter size of a penile organ, and to place the magnetic field created by the placement of the magnets closer to tissue portions on a penile organ, for greater therapeutic and medical effect.

It will, therefore, be understood that substantial and distinguishable structural and functional advantages are realized in the present invention over the prior art devices; and that the present invention's novel structure, diverse utility, and broad functional applications, in comparison to the prior art, serve as important bases of novelty and distinction in this regard.

SUMMARY OF THE INVENTION

The foregoing and other objects of the invention can be achieved with the present invention, device, assembly and functional method of use; which is a magnetic therapeutic penile band for use in uniform pressure and size-responsive contact and interaction with areas on a penile organ, and in interaction with physiological dimension and size changes of such an organ. The magnetic therapeutic penile band of the present invention is provided with a support band of partial flexible construction having first and second ends and first and second perimeter portions; and the structural capacity and means for containing, compartmentalizing, or pocketing, a number of separate magnetic portions. The invention is provided with a plurality of magnetic portions, each of which has one or more components having a positive area, substantially positive (South) in magnetic field charge; and a negative area, substantially negative (North) in magnetic field charge. Each of the plurality of magnetic portions is mounted and pocketed on the support band so that each is serially aligned and spaced, and oppositely charged in adjacent positional relation to one another. The invention is also provided with structural means for coupling the first and second ends of the support band. Therefore, by virtue of the above recited structural and functional elements and means, the magnetic therapeutic penile band is installable about or around a preselected location on a penile organ in a contacted manner; and is self-adjusting to, while remaining in uniform pressured contact with, a penile organ in its flaccid state and in its dimensionally changing and erectile state, while providing a magnetic field to all adjacent tissue areas in relation to where the invention is installed on a penile organ. The invention, thereby, changes, automatically, in perimeter or circumferential size to accommodate such size changes in a penile organ, whether larger or smaller in dimensional magnitude, without substantially increasing in its contacted pressure against a penile organ.

REFERENCE NUMBERS IN DRAWINGS

Figure 5:
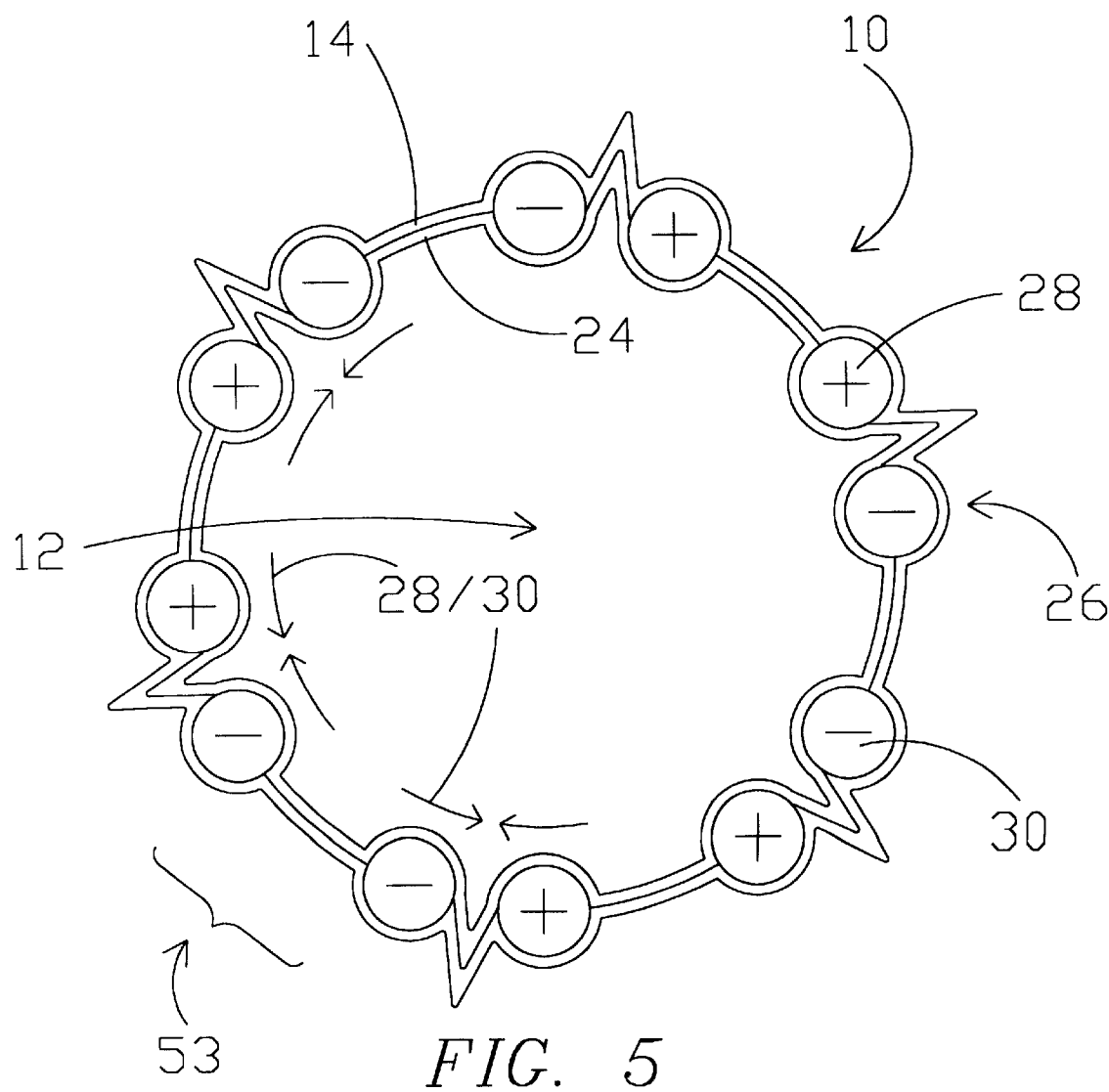
FIG. 5 is an enlarged elevated side perimeter view of the invention of FIG. 1, in a generally unexpanded, contracted or smaller positional configuration similar to the invention's positional state when installed on, or in interaction with, a dimensionally smaller or flaccid penal organ, with which the invention interacts.
Figure 8:
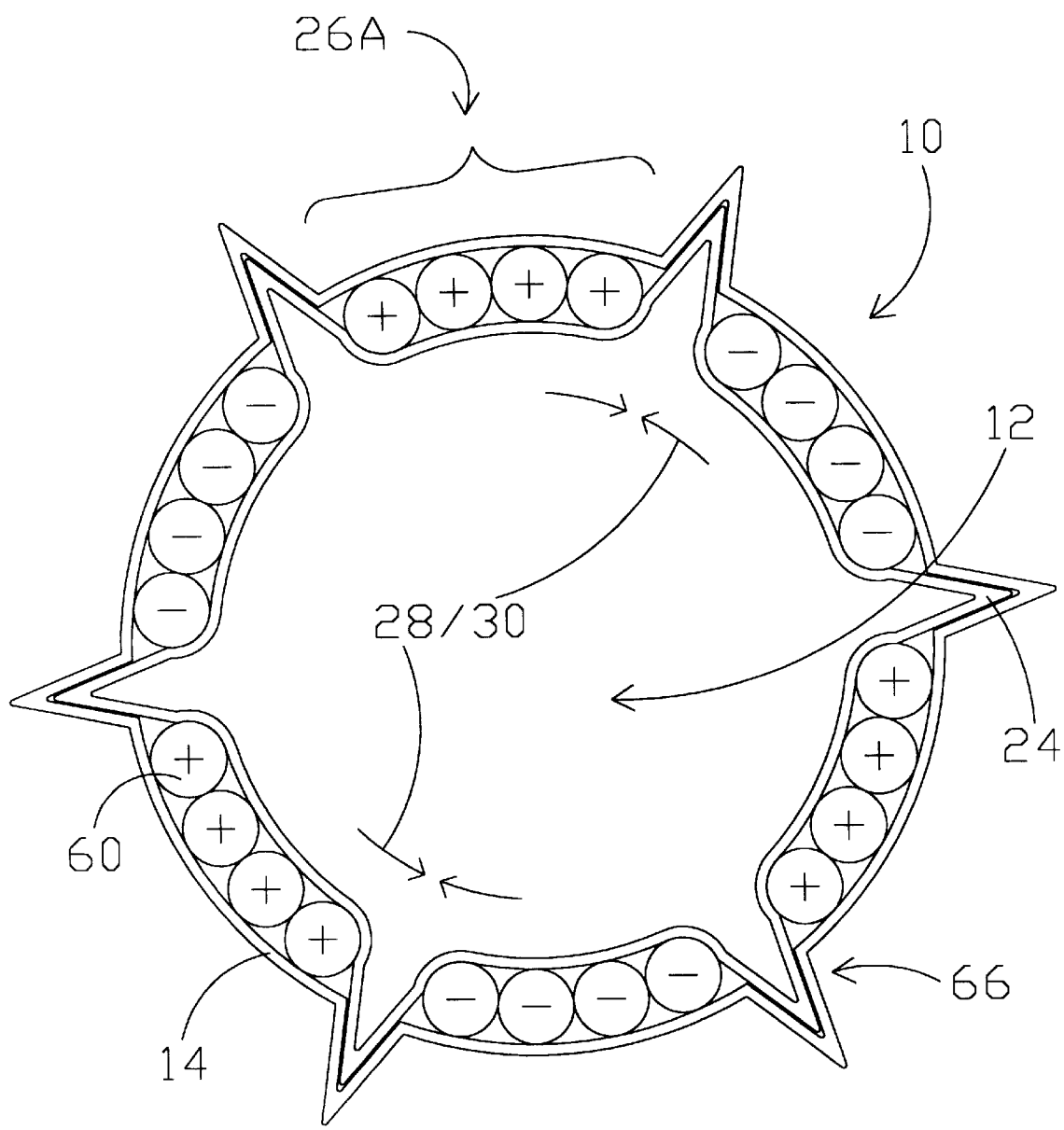
FIG. 8 is an enlarged elevated side perimeter view of the invention, of FIG. 6, in a generally folded/corrugated, unexpanded, contracted, or smaller positional configuration, similar to the invention's positional state when installed on a dimensionally smaller or flaccid penile organ, with which the invention interacts.
Figure 10:
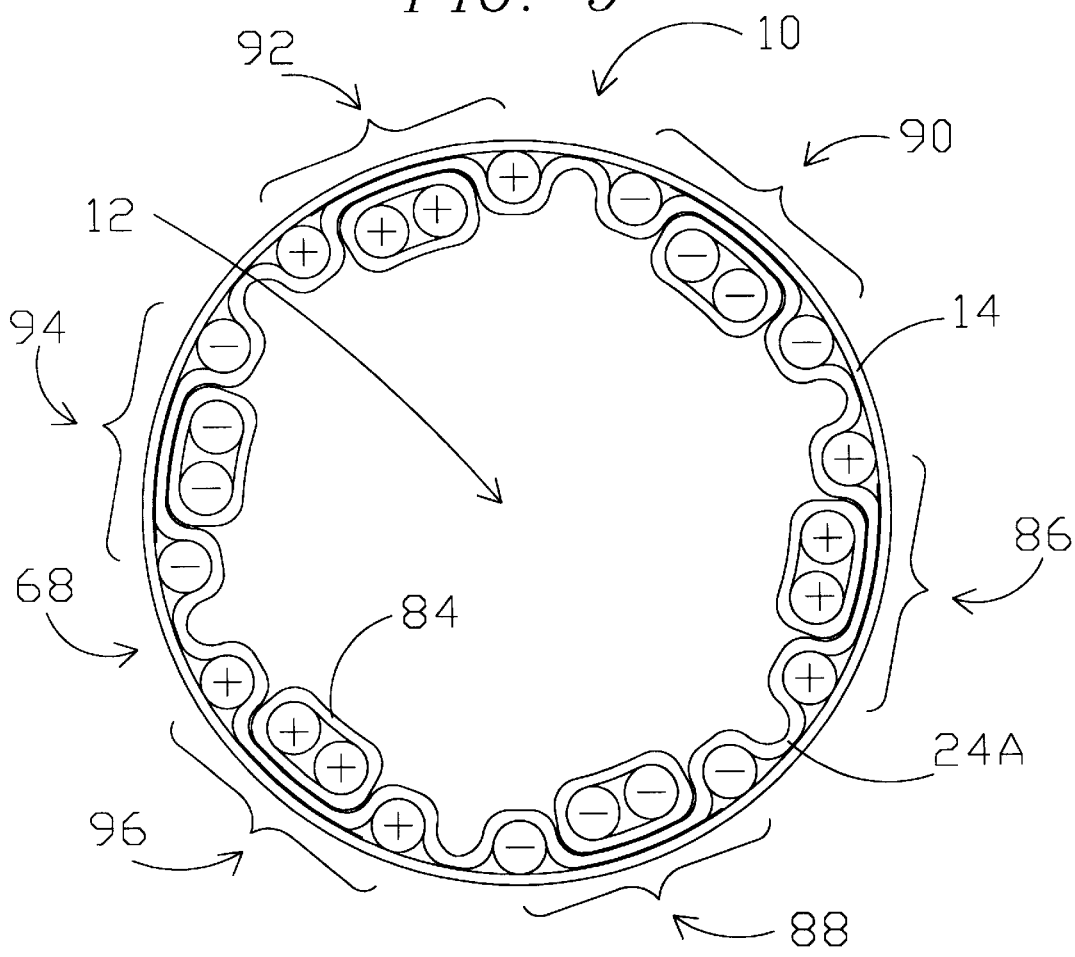
FIG. 10 is an elevated side perimeter view, reduced in scale, of the invention of FIG. 9, in generally enlarged or expanded positional configuration, similar to the invention's positional state when installed on a dimensionally enlarged or erectile penile organ, with which the invention interacts.
Figure 11:
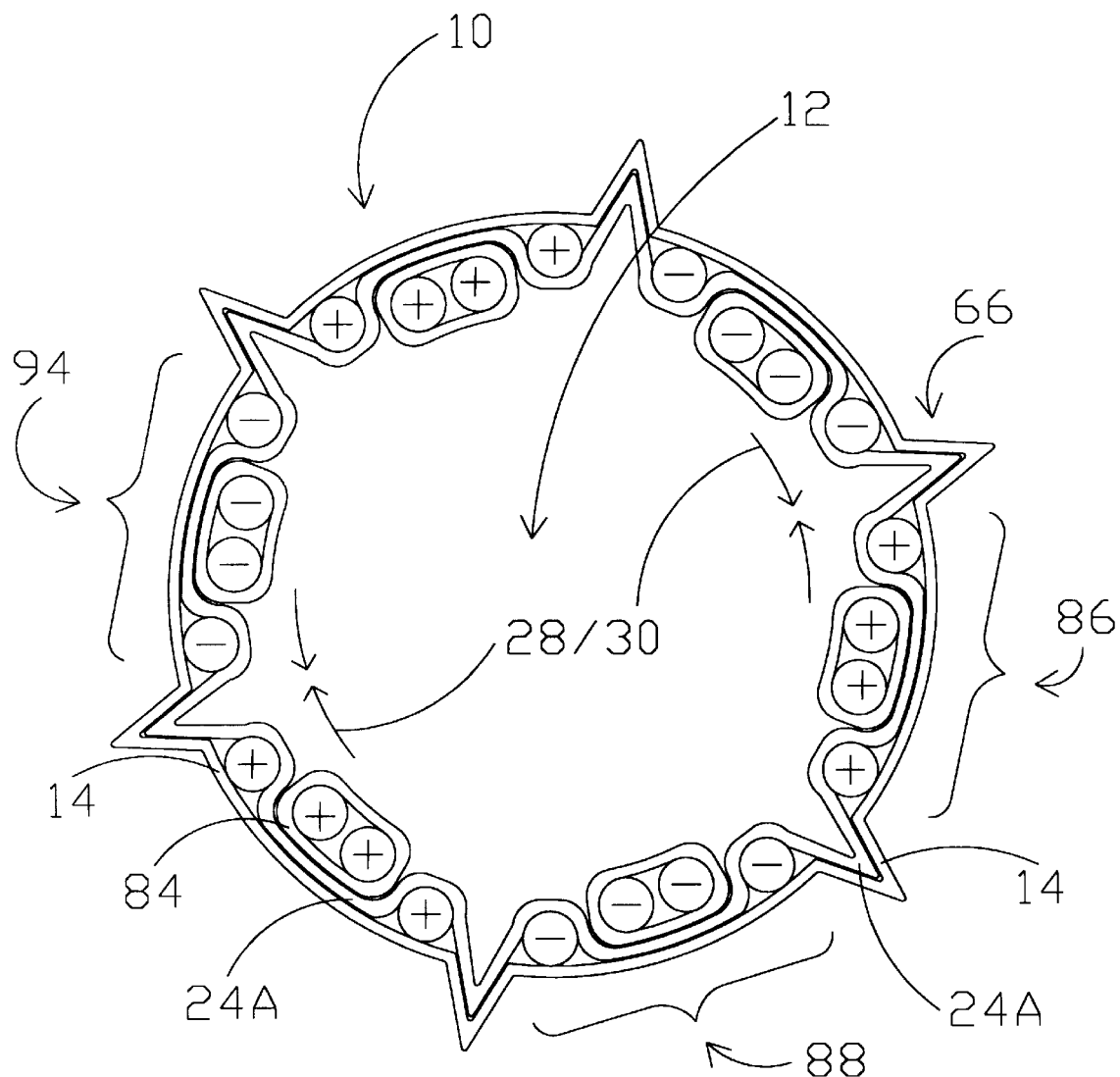
FIG. 11 is an elevated side perimeter view, reduced in scale, of the invention, of FIG. 9, in a generally folded, unexpanded, contracted, or smaller positional configuration, similar to the invention's positional state when installed on a dimensionally smaller or flaccid penile organ, with which the invention interacts.

10 Magnetic Therapeutic, Self-Adjusting Penile Band Assembly or TPA (Therapeutic Penile Assembly) of the present invention.
12 penis or penile organ, with which the present invention interacts
14 support band
16 first end of (14)
17 lengthwise axis of (14)
18 second end of (14)
20 first perimeter portion of (14)
22 second perimeter portion of (14)
24 pocketing layer subassembly of (14)
26 magnetic portion members
28 positive ("+") area of (26)
29 lengthwise axis of (26)
30 negative ("−") area of (26)
32 coupling subassembly
34 inboard surface of (14)
36 outboard surface of (14)
38 widthwise perimeter portion of (14)
40 further widthwise perimeter portion of (14)
42 first end of (24)
44 second end of (24)
46 inboard surface of (24)
48 outboard surface of (24)
50 first magnet
52 second magnet
53 spaced pairings of magnets
54 collar portion
56 collar lumen
26A magnetic groupings (another embodiment)
60 individual magnet components of (26A)
28A positive (+) end of (60)
30A negative (−) of (60)
66 folded portions
68 spacing portions
26B magnetic groupings (another embodiment)
70 magnet components of (26B)(26C)
28B positive (+) end of (70)
30B negative (−) end of (70)
24A biasable mesh layer (another embodiment)
80 first end of (24A)
82 second end of (24A)
84 intra-magnet retainer layers
86 first magnetic grouping of (26B) (FIGS. 10 and 11)
88 second magnetic grouping of (26B) (FIGS. 10 and 11)
90 third magnetic grouping of (26B) (FIGS. 10 and 11)
92 fourth magnetic grouping of (26B) (FIGS. 10 and 11)
94 fifth magnetic grouping of (26B) (FIGS. 10 and 11)
96 sixth magnetic grouping of (26B) (FIGS. 10 and 11)
98 first individual magnet component of (26B) (FIG. 9)
100 second individual magnet component of (26B) (FIG. 9)
102 third individual magnet component of (268) (FIG. 9)
104 fourth individual magnet component of (26B) (FIG. 9)
106 first end magnet position of (26B) (FIG. 9)
108 second end magnet position of (26B) (FIG. 9)
26C magnetic grouping with retainer layers (84) (another embodiment-FIGS. 18 & 19)
110 securing means (FIGS. 18 and 19)
28/30 positional arrows (attracting oppositely charged magnetic components) (FIGS. 5, 8 & 11)

DETAILED DESCRIPTION OF THE PREFERRED EMBODIMENTS OF THE INVENTION

The following description of the preferred embodiments of the concepts and teaching of this present invention is made in reference to the accompanying drawing figures which constitute preselected illustrated examples of the structural and functional elements of the invention, among many other examples existing within the scope and spirit of the present invention.

Referring now to the drawings, FIGS. 1, 2, 3, 4, 5, 4A, 5A, 6, 7, 8, 9, 10, 11, 13, 14, 15 and 16; thereof; there is shown a magnetic therapeutic, self-adjusting, penile band assembly 10 of the present invention, referred to herein as the TPA (or Therapeutic Penile Assembly), 10, of the present invention.

The TPA 10 is intended to be utilized in biasable (or pressure-imposing) interaction with a human or animal penis or penile organ 12, by virtue of comfort fitting in relation to areas on a penile organ, and in responsive interaction to the physiologically induced, or other, changing dimensions, size and/or circumferential or cross-sectional magnitude or perimeter of a penile organ 12.

The TPA 10 is of flexible and stretchable, and/or biasable, fabricated construction; and provided with the support band 14. The band 14 is characterized by having first and second ends, respectively, 16 and 18, first and further perimeter portions, 38 and 40 respectively; and the pocketing layer subassembly 24 of biasable construction for pocketing, compartmentalizing and retaining, as its general function within the invention, a number (or plurality, more than one) of separate magnetic portions (described in more detail herein), as shown in FIG. 1 and other drawing s herein.

Figure 1:
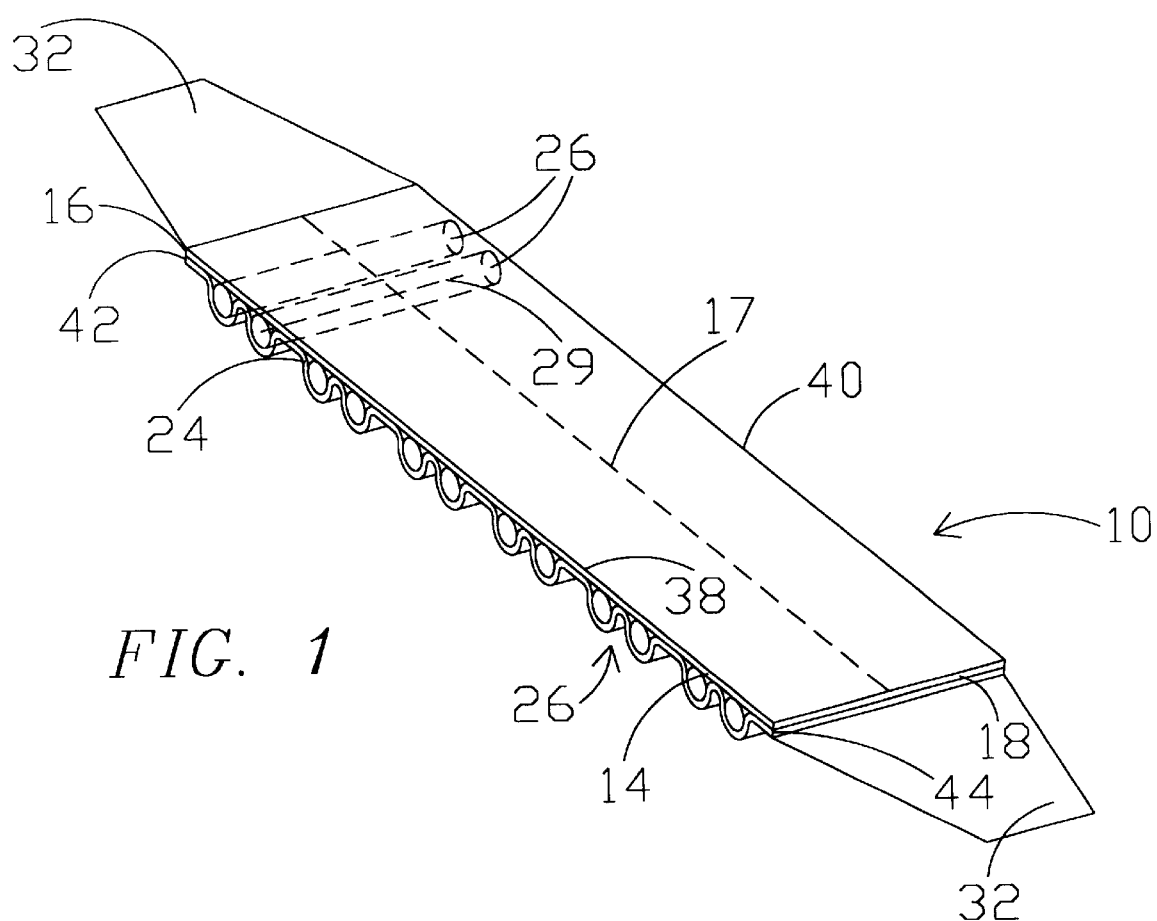
FIG. 1 is a perspective view of one preferred embodiment of the novel magnetic therapeutic penile band device showing by broken lines the underlying position of subportions of two magnetic portions.
Figure 1A:
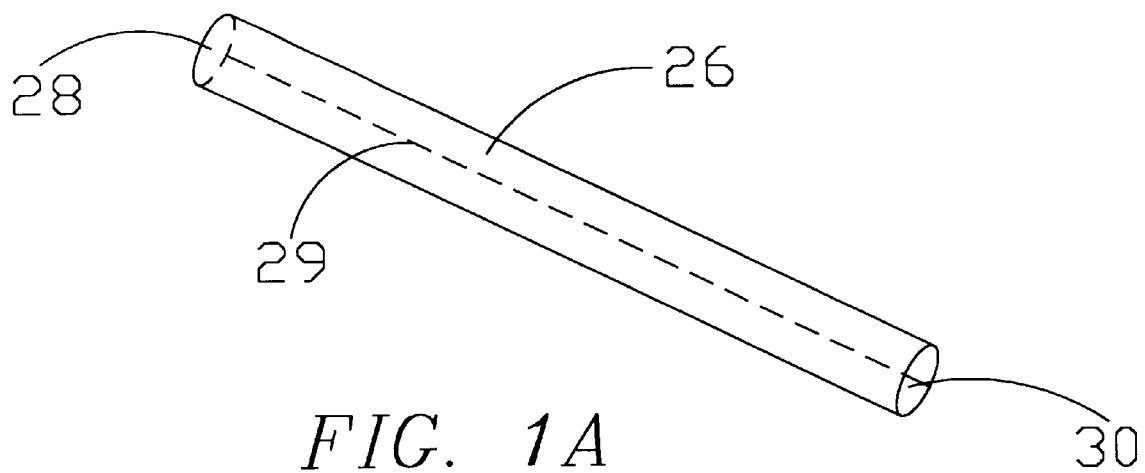
FIG. 1A is a perspective view of a general exemplar of one of the individual magnet component used and a part of FIG. 1, symbolized as to "+" (positive) and "−" (negative) charged portions.
Figure 2:
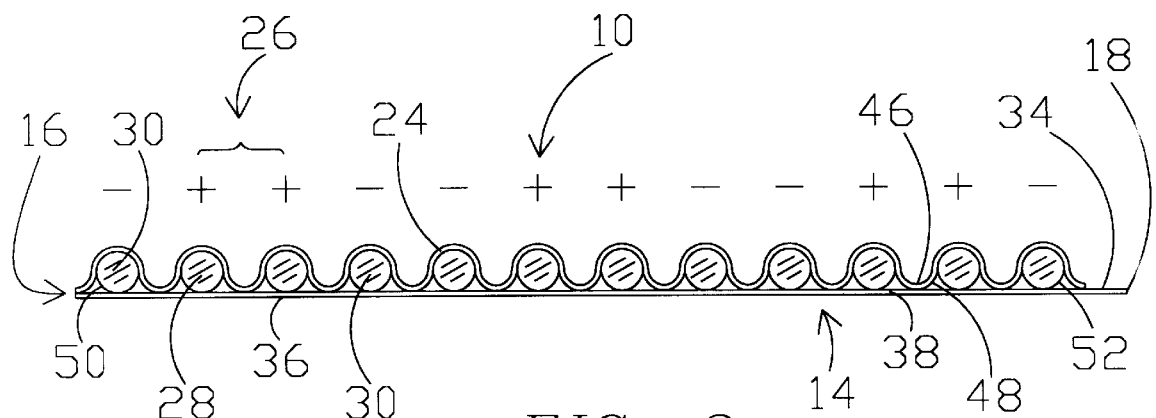
FIG. 2 is an enlarged side perimeter view of the magnetic therapeutic penile band and invention, of FIG. 1, in an expanded positional configuration; illustrating positive and negative magnetic field polarities by "+" and "−" symboling; as utilized throughout the drawings of this application.

The TPA 10 is provided with a number of magnetic portions 26, shown by example IN FIGS. 1 and 2. Each magnetic portion is provided with the positive area 28, and the negative area 30.

For purposes of definition, convention and/or reference herein, in terms of the relationship between different or opposing magnetic charges, poles, domains or entities; the positive area 28 is, substantially, in magnetic terms considered or deemed to be the 'South' polarity or pole of a magnet or group of magnets together; and the negative area 30 is substantially, in magnetic terms, the 'North' polarity or pole. This convention is in relative accordance with texts addressing the subject of magnetism which state that: Since a magnet always aligns (or lines) itself up with the earth's magnetic north pole, that there seems to be some definite laws governing magnetic effects, these being the laws of attraction and repulsion; and that the attraction and repulsion laws of magnetism are substantially the same as those of electric charges, except that "North" (N) and "South" (S) polarities are used (in reference) instead of "negative" and "positive;" the magnetic laws being that in this relative context, that 'like poles repel,' and that 'unlike poles attract.'

In preferred embodiments of the present invention, each of the magnetic portions 26 are mounted in compartmentalized or pocket-like/pouched support arrangement on the support band 14. In positional relationship to one another, each magnetic portion 26 is aligned in series, or consecutive (one-coming-after-the-other) relation to one another. In this serial alignment, each of the magnetic portions 26 is spaced or distanced from one another, or are positioned and/or mounted so that they have some spacing between them; and each magnetic portion 26, in relation to its adjacent serial, neighboring magnetic portion 26, is substantially different (or opposite) in overall magnetic polarity or charge.

The TPA 10 is also provided in these preferred embodiments with the coupling subassembly 32, attached to the support band 14 for attaching and coupling its first and second ends 16 and 18. The TPA 10 is, therefore, installable about or around a desired location or site on a penile organ 12; and is self-adjusting in responsive positional relationship to, while remaining in contact with, the penile organ 12; while in its physiologically, smaller or flaccid state or condition, and in its larger, dimensionally changing, larger, or erectile state or condition. During these size or dimensional changes of the penile organ 12, the TPA 10 continues to provide a magnetic field comprising, or of, opposing North (negative) and South (positive) polar entities, circumventing, or peripherally around, the installation site of the TPA 10 on the penile organ 12.

In preferred embodiments, therefore, the TPA 10 is utilized in installed interaction with a penile organ 12, such as a human or other mammal or other animal penis; i.e., the penile organ 12 constitutes no actual part of the present invention, but is simply that which the invention is designed for use in interaction with. The TPA 10 is preferably constructed or fabricated to flexibly and comfortably make contact with the penile organ 12, during its physiologically, or other, responsive, cross-sectional and dimensional changes; and to contemporaneously provide a magnetic field, when installed, to adjacent areas on the organ 12, for the purpose of improving the flow of blood circulation and for functional improvement of tissue portions within or a part of the penile organ 12, such as muscles, erectile tissue, skin and subcutaneous tissue areas.

The positional and charge relationship of the magnetic portion members 26, and their securement on the band 14, therefore, allows the band to become larger or smaller in perimeter or circumference, in response to such changes of a penile organ 12, with which the invention interacts; each, without substantial change in the biasing force or pressure exerted on the penile organ 12. This assures that the TPA 10 of the present invention will not place too much inward or inboard pressure from the band 14 or its securing layers, on the penile organ 12, while changing size in response thereto; or, cut off or negatively affect blood flow through such an organ.

The coupling subassembly 32, can, in and of itself be integral in construction, forming an attachment, of many diverse types, between the first and second ends 16 and 18 of the support band 14 and/or the first and second ends 42 and 44 of the pocketing layer 24. In this regard, the coupling 32, in preferred embodiments of the invention, can be fabricated, constructed, or manufactured in a hook and loop assembly, or VELCRO®-like assembly, encompassing or interfacing ends 16 and 18 and/or 42 and 44. It will be understood by those skilled in the art that other structural means can be employed in construction of the coupling 32. However, all such means must assure a secure and comfortable installation fit of the TPA 10 (in preferred embodiments thereof), and its band 14 over a penile organ 12 in such a manner as to facilitate (and not impede) the functional action of the band 14, the layer 24 and the magnetic members 26, with regard to the self-adjusting feature and the contemporaneous magnetic field or magnetic differential feature of the present invention.

The pocketing layer 24, in the form of a biasable matrix layer, as described herein, in preferred embodiments, is attached to the support band 14 in a manner where the inboard surface 34 of the band 14 opposes, or is positionally adjacent or generally interfaced with the out board surface 48 of the layer 24.

In preferred embodiments, the magnetic portion members 26 can take the form of individual magnet members, or magnets; and the form of multi-component magnet members, or a number of magnets adjacent or in magnetic or positional relationship to one another within a respective magnetic portion 26. The portion 26 can also take the form of one, single, individual magnet, or relatively larger or smaller combinations of magnet components, members or entities.

However, the relationship between each magnetic portion member 26 is one of opposite adjacent charge; while all individual magnets within or a part of an individual respective magnetic portion 26 are of the same magnetic charge, or positionally aligned to constitute substantially the same magnetic charge at their ends as aligned; as illustrated, by example, in FIGS. 2, 3, 4, 5, 5A, 6, 9, 10, 12, 12, 14, 15, 16, and other drawings herein.

In additional preferred embodiments of the present invention, the support band 14 is viewed as having, in position a lengthwise axis 17, as shown by example in FIG. 1, between the first end 16 and the second end 18 of the support band 14. The band 14 is also provided with the inboard surface 34 and the outboard surface 36; and the widthwise perimeter portion 38 and further widthwise perimeter portion 40.

The plurality or number of magnetic portions 26 in these preferred embodiments are practiced, within the scope and spirit of the present invention, and take the form of a plurality of magnet members; each of which is provided with its positive end 28 and negative end 30 (first and second ends, respectively); and its lengthwise axis 29 on which each of the ends 28 and 30 are separated and oppose one another positionally; as shown in FIGS. 1, 1A, 2, 4 and 4A.

As illustrated, in these embodiments, each of the magnetic portions 26 (magnet members) is positioned in adjacent series (serially); or positionally, one-after-the-other; on the inboard surface 34 of the support band 14 so that its lengthwise axis 29 is generally parallel, and a spaced area or distance, from the lengthwise axis 29 of another adjacent magnetic portion 26; and is also positioned in this regard so that each lengthwise axis 29 of each of the respective serially adjacent portions 26 is generally positioned in a positionally transverse relationship to the lengthwise axis 17 of the band 14.

The pocketing layer subassembly 24 of the support band 14 takes the form, in these embodiments, of a biasable matrix layer. The pocket layer 24, in this form, as practiced as a part of the invention, is provided with first and second ends, 42 and 44, respectively. The layer 24 is attached to the support band, by virtue of attachment means, including, but not limited to, stitching, polymer; fabric, glue, and/or cement means; or by virtue of integral fabrication or construction. The layer 24 is fabricated from construction materials, and attached to the band 14, so that it is characterized in function, as a part of the TPA 10, as having flexible, and shape responsive, contracting and expanding qualities, when installed in contacted interaction with a penile organ 12.

In preferred embodiments, the support band 14 is fabricated from a number of flexible, foldable and bendable construction materials. In this regard, some preferred materials include, without limitation, at least partially expandable ribbon-like material, tape-like material, elastic polymer and resilient flexibly biasable substances. Although many different configurations can be utilized, one general preferred shape, illustrated by example in the drawings as the band 14, and other layers described herein, is 'strip' or rectangularly-shaped configuration or visual shape.

The pocketing layer subassembly 24, in the form of a matrix layer, in preferred embodiments, is provided with the inboard surface 46 and the outboard surface 48; as illustrated by example in FIGS. 1, 2, 3, 4, 5, 4A and 5A. The layer 24 is preferably fabricated from contractable and expandable mesh fabric material, although other construction material having similar elastic dynamics or other similar characteristics can be utilized in the present invention. The layer 24 is fabricated or constructed, shape-wise or configurationally, to preferably interface dimensionally, or be generally concurrent at its perimeters, with the support band 14; although smaller or larger dimensioning can be employed in this regard within the present invention.

Additionally, in preferred embodiments, the pocketing layer 24 is fabricated from a flexible, meshed, magnetically neutral fabric or constructive material, such as power net, stretch Lyera lining, elastic mesh material; or other mesh material having respective band, sub-fabric components, to place respective biasing pressure on skin and/or underlying tissue of a penile organ 12; or other stretchable, unitary fabric material, compatible or user-friendly with respect to magnetic materials utilized in the construction of the magnetic portion members 26.

In related preferred embodiments of the invention, illustrated, each of the magnet components or magnets, comprising the respective magnetic portion members 26 is flexible and resilient, and cylindrically-configured in shape.

In preferred embodiments, the magnetic portion members 26 are chosen from some several types of cylindrical, rod, or linear square-like, magnetically and physically resilient, flexible magnets; such as, for example, the "Sintered Alnico 5" magnet material manufactured by Adams Magnetic Products Company, 7061 Grand National Drive, Orlando, Fla. 32819 (and other locations); and also ceramic magnetic material and some several of their diverse line of magnetic products; and magnetic material manufactured by Bunting Magnetics Company, 500 S. Spencer Avenue, Box 468, Newton, KS 67114 (and other locations). Additionally, in this regard, a number of diverse types of small magnets with low 'gauss' values, manufactured by a number of companies or concerns, can be effective and functional, as the magnetic portion members 26, or as part or component parts thereof in the present invention. Additionally, a number of other types of magnets can be utilized in the construction of the magnetic portion members 26 to bring about a magnetic differential, and magnetic positional relationships, to create a therapeutic magnetic field, interfacing a penile organ 12, within the scope of the present invention.

Figure 3:
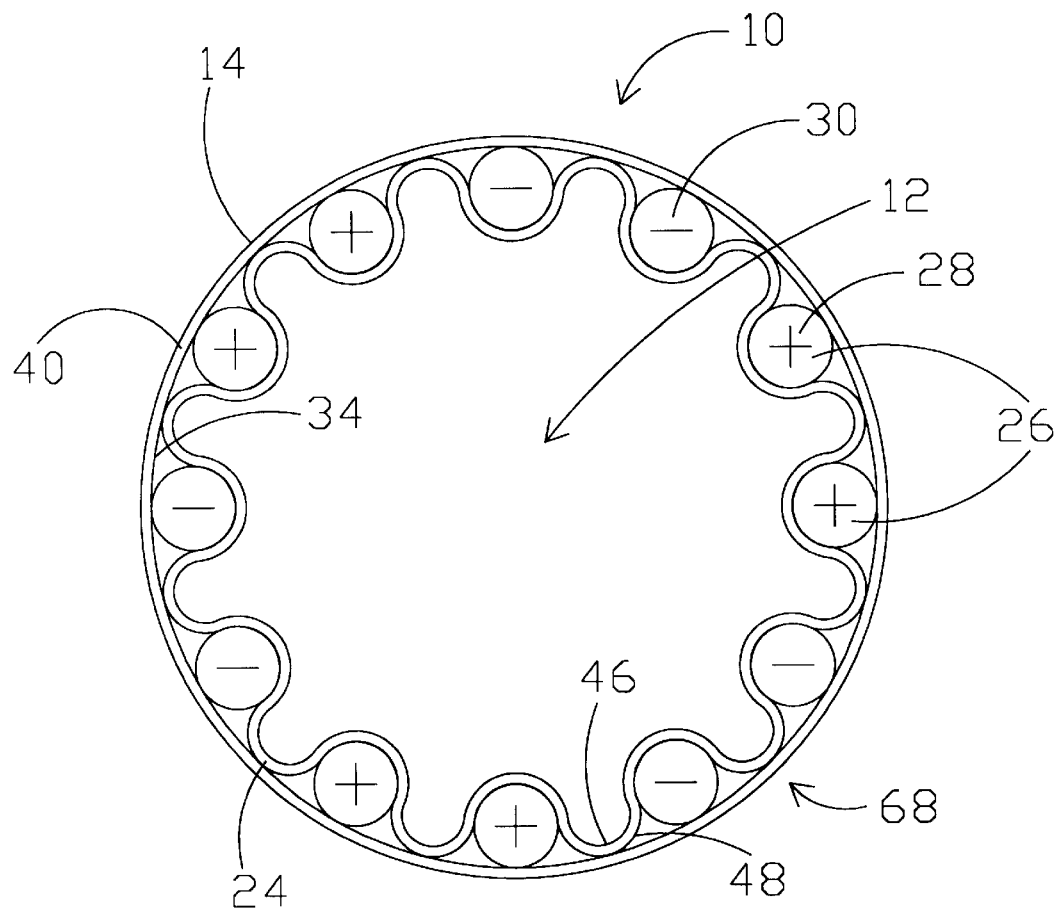
FIG. 3 is an enlarged elevated perimeter view of the invention of FIG. 1 in a generally enlarged and expanded positional state similar to the invention's positional state when installed on a dimensionally enlarged or erectile penal organ, with which the invention interacts.
Figure 4:
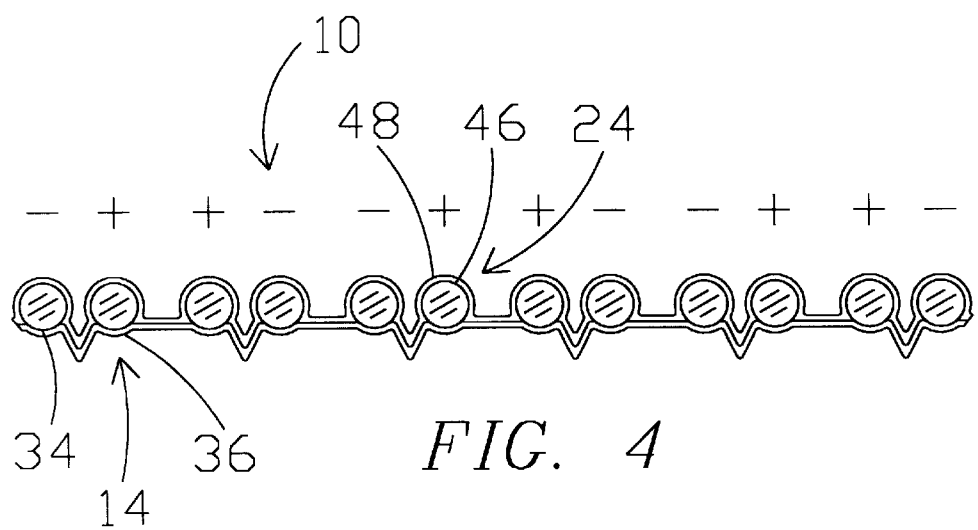
FIG. 4 is an enlarged elevated side perimeter view of the invention of FIG. 1, in a contracted or substantially nonexpanded positional configuration realized by use and interaction of the present invention.

In this regard, a preferred embodiment thereof utilizes the magnetic portion members 26 in the form of a plurality or number (>1) of magnet members. In this embodiment form the magnetic members 26 are provided with the first magnet 50 which is positioned on the support band 14 and individually pocketed and secured by the pocketing layer 26 thereon; as illustrated in FIGS. 2 and 3. The negative area 30 of magnet 50, in this embodiment, is positioned adjacent or proximate to the widthwise perimeter portion 38 of the support band 14; and the lengthwise axis 29 of magnet 50 is facing, and/or adjacent, proximate or parallel to the first end 16 of the band 14.

In this embodiment, the magnetic members 26 are also provided with the second magnet 52 which is positioned on the band 14 and individually pocketed and secured by the pocketing layer 26. The negative area 30 of magnet 52 is positioned adjacent or proximate to the widthwise perimeter 38 of the band 14, similar in this regard to the positioning and securement of magnet 50. The lengthwise axis 29 of magnet 52 is facing, adjacent and/or generally parallel to the second end 18 of the band 14.

The magnetic members 26, in this embodiment, are further provided with a number or plurality (first and further) spaced pairings of magnets 53, positioned and secured in series on the band 14, between the first magnet 50 and the second magnet 52; as illustrated, by example, in FIGS. 2, 3, 4, 5, 4A and 5A. This plurality of spaced pairings 53 can be from two (2) to ten (10) in number, or more, depending on the desired magnetic field effect or magnetic differential desired and the size or dimensions of the magnets or magnetic components utilized. One such preferable number of such pairings 53 is five (5) (or a total number of 6 pairings 53), positioned on the band 14 and pocketed and secured by the layer 24, as illustrated. In this regard, each of the spaced pairings are positioned in series (serially) between the first magnet 50 and the second magnet 52.

As illustrated, each space pairing 53 has two magnets or magnet components which are positioned and secured by the band 14 and layer 24, and are adjacent or proximate to one another while being spaced and having a dimensional distance between one another. And in this positional relation to one another, each of the two magnets of the spaced pairing 53 is compartmentalized and individually covered and contained by a separate pocketing formed between the band 14 and the layer 24; and each of the two magnets is positioned within a given spaced pairing 53 so that the same end or area, either positive or negative (in substantial magnetic charge), 28 or 30; is positioned adjacent or proximate to the widthwise perimeter 38 of the band 14; thus, presenting the same magnetic charges at adjacent ends or areas (28 or 30), as positioned, while constituting different magnetic charges as between, or in relation to, each adjacent pairing 53.

Therefore, in this embodiment, each of the respective spaced pairings 53 is opposite in magnetic charge in relation to its adjacent neighboring spaced pairing 53, as illustrated by example, in the drawings herein. It will, therefore, be understood that spaced pairings 53 of opposite occurring positive and negative magnetic charge continue along either widthwise perimeter, 38 or 40, of the support band 14, when the first and second ends, 16 and 18, of the band 14 are connected to one another, as illustrated in FIGS. 3, 5 and 5A.

Figure 4A:
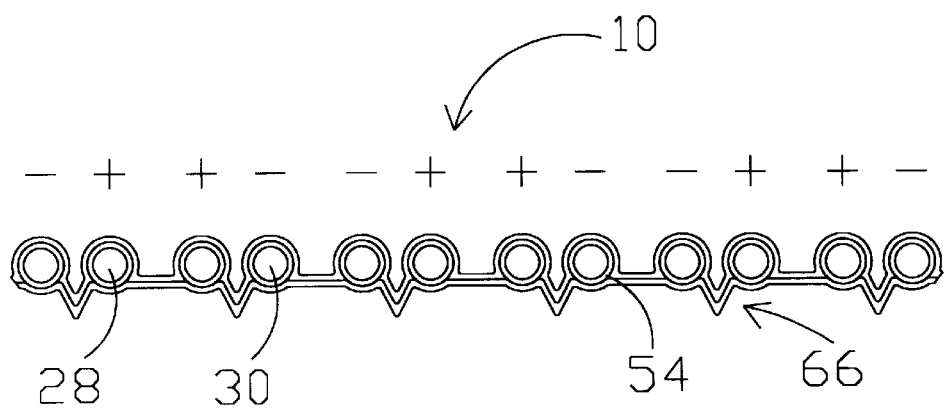
FIG. 4A is another embodiment and view of the view and embodiment of the invention, of FIG. 4, illustrating therein the invention's magnet sheath or collar components.
Figure 5A:
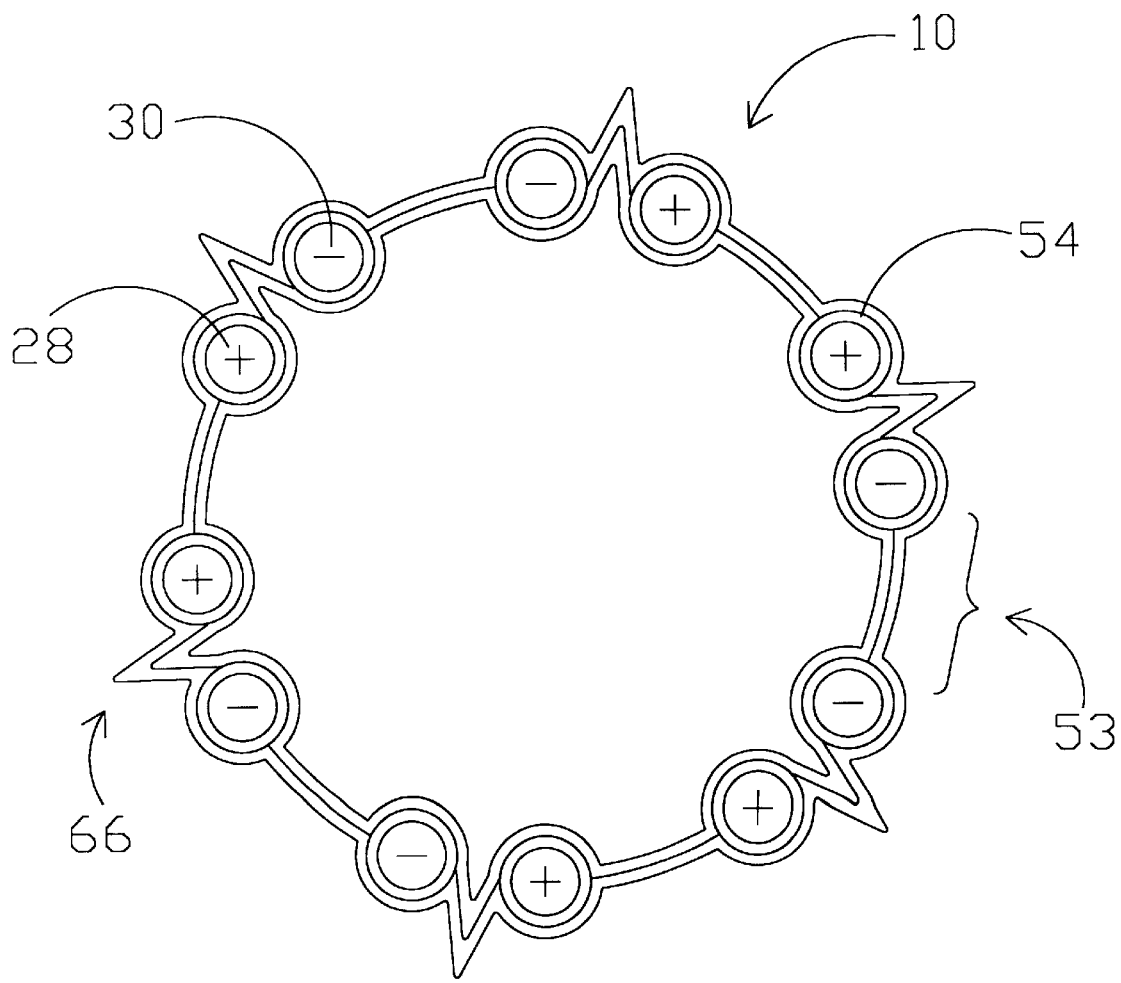
FIG. 5A is another embodiment and view of the view and embodiment of the invention of FIG. 5, illustrating in addition, therein, the invention's magnet sheath or collar components.
Figure 17:
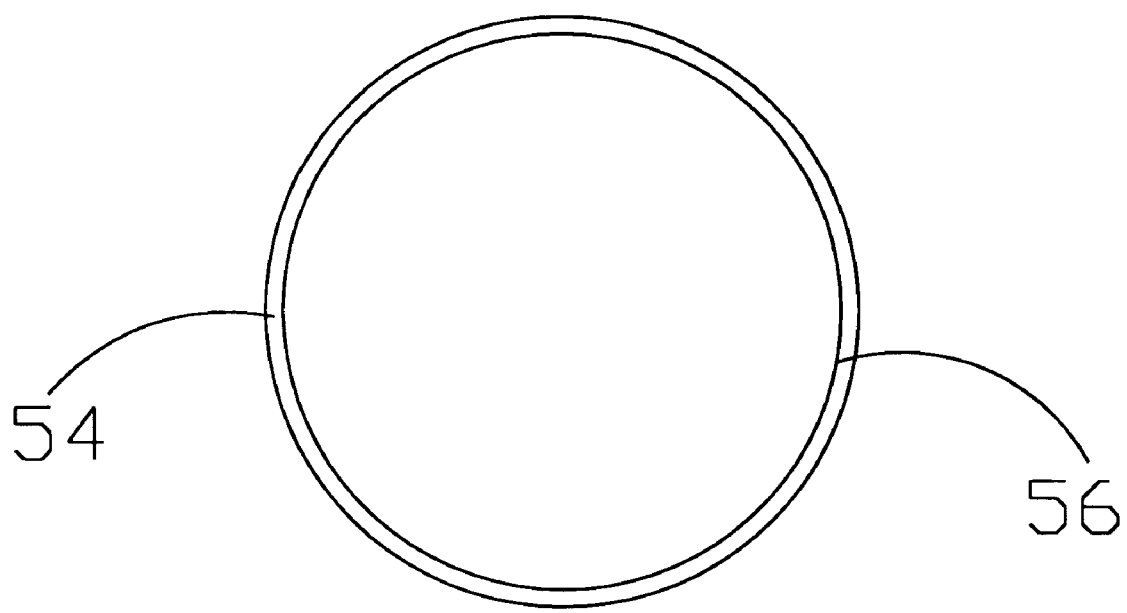
FIG. 17 is an end view of one of the exemplar individual magnet components utilizable in the present invention, illustrating a sheath or collar member, of the present invention, overlying the lateral portions of the magnet component.

In preferred embodiments, each of the magnetic portion members 26, and the various forms that these members may take within the scope of the invention in so far as individual or multi-component magnet members, is provided with a collar portion 54, or sheath member, as illustrated by examples in FIGS. 4A, 5A and 17. In this regard, although the collar 54 is shown in positional relation to a cylindrical magnet in FIGS. 4A and 17; it is within the invention's scope to utilize individual magnets within the magnetic members 24 and installed collars 54 of many different cross-sectional configurations; including, without limitation, elliptical, parabolar', linear, square, rectangular, triangular, or multi-arced or multi-faced cross-sectional configurations. In this regard, cylindrical, circular, and elliptical or cam-like configurations have worked well as preferred embodiments, within the scope of the invention; and are illustrated as examples thereof in the drawings, without limitation as to other acceptable configurational utilization within the scope and spirit of the present invention.

Additionally, in these related preferred embodiments of the invention, the collar portion 54 is provided in a cylindrical-like configuration, and a circular or elliptical cross-sectional shape; although other shapes and configurations can be utilized. The collar 54 has and defines internally, there within, a collar lumen 56 along at least one of its length portions, from one of its ends to the other; as shown, by example, generally, in the referenced drawings. In these embodiments each of the magnet components of the magnetic portion members 26, shown by example, is slid and firmly held in an installed position within the lumen 56; and, likewise, is also retrievable or withdrawable, if so desired, from the lumen 56. Although it will be understood in this regard that, within the scope of the invention, each of the components of the magnetic portions 26 can be fabricated or constructed already permanently fixed or integrally installed within the lumen 56 of the collar 54, for use as a part of the invention.

Advantages presented in these preferred embodiments of the invention include the ability of more accurately utilizing the thickness of a selected plastic or rubber-sleeved, collar 54, installed around each magnet component, plus the thickness of the fabric securing layer to install and secure the respective magnets about one-quarter inch (¼") apart, with about ½ inch between portion members 26. Additionally, the utilization of the collar 54, encapsulating each magnet component, prevents the such individual magnets from directly coming in contact with each other to, in effect, become one magnet. Also, the plastic or rubber collar 54 creates a space between each magnet, so there is a magnetic field between each neighboring magnetic component. The collar 54 also facilitates the added functional utility of allowing placement of shorter or longer individual magnetic components within a magnetic portion 26, to provide more bendability' or flexibility in such selected areas around the perimeter of the band 14 or securing layers where long and short magnetic components are utilized.

Also, in this regard, it is also within the scope and spirit of the present invention to utilize, or utilize selectively or respectively, each of the magnet components of respective magnetic portion members 26, without the collar 54, or other envelope-like lining, or other type of specific covering, or covering-like means; in selected situations and in preferred embodiments.

Additionally, with regard to constructive materials of the collar portion 54, when this element or member is employed in preferred embodiments of the invention; such materials can be chosen from light polymer or plastic material (of drinking straw-like thickness), rubber material or mixture, fabric, or other material or substances which are 'magnetically-friendly' (or non-interfering), and not burdensome and/or substantially detracting or limiting from the described or expressed, intended purposes and use in the present invention of therapeutic magnetic differential and magnetic field application to penile organ tissue; and the novel process and system inherent in this present invention.

As illustrated, by example, six (6) spaced pairings 53 of magnetic portion members 26, are utilized; and six such groupings including one (1) to four (4) individual magnets or magnet members (as previously discussed and later covered herein) can be utilized in several preferred embodiments of the invention. The role of the six sets or groupings of magnets (or other preselected number), positionally placed as described; of attracting one another (in the contraction/expansion process) in response to the changing dimensions of a penile organ is very important, within the scope of the invention. It brings about, in combination with the support band 14 and pocketing layer subassembly 24 (and other magnet securing layers discussed herein), upon which the magnets are secured, the attraction/contraction process which facilitates automatic adjustment of the band 14 in its responsive contact with a penile organ 12, experiencing nightly or other erections or erectile states.

As in each of the embodiments of the present invention, set forth herein; it is preferred that each magnetic element of magnetic portion 26, pairing 53, and/or other magnetic set, grouping, components or series described herein (26A, 60, 26B, 70, 86–96 and/or 98 & 100), be aligned parallel to one another, or each other, at a preferably calculated distance apart. This desired distance apart will allow each set of attracting magnets of the six sets (or other number) utilized, to pull apart, or disengage, when a slight pulling force, such as that caused by the enlarging and erection of a penile organ, is present; as illustrated by example in FIGS. 3, 7, 10 and 12. This also facilitates a situation when no, or little, pressure (or pulling force) is present (based on the fitting of the TPA 10 on a penile organ 12); i.e., when the penile organ has lost its erection-state or becomes flaccid; such that the interfacing portions 26, pairings 53, or other respective magnetic sets/groupings described herein, which would normally attract each other (being of opposite charge in relation to one another), pulling and attracting towards each other; positionally orienting such groupings of magnets back in close, attached position, end-to-end; as illustrated, by example, in FIGS. 5, 5A, 8, 11 and 12.

In accordance with teachings of the invention, the preferred attraction-magnitude and force between portions 26, pairings 53, or lateral end portions of groupings of magnets described as a part of the invention herein; is based on the distance apart of such magnet sets and the strength of individual magnetic elements utilized therein.

In working examples of the TPA 10, the magnetic portion members 26, spaced pairings of magnets 53, magnetic groupings 26A and the magnetic groupings 26B are; each; preferably one-half inch (½") apart; with the individual magnets or magnetic components, each, therewithin, being five-eights inch long in substantial or general length. In this regard, individual magnets utilized are preferably "Alnico 5"® individual magnets (further described herein), generally cylindrically-shaped, and magnetized by length (i.e., one lengthwise end being substantially positive ["+"] in magnetic charge or pole, and the other opposite lengthwise end being substantially negative ["−"] in magnetic charge; as described and illustrated herein).

The action of the six (6) sets of attracting magnets (as described and illustrated herein); or, preferably, selectively, from 3 to 12 sets of groupings of magnets, described herein, are important and novel elements of the present invention. It is the positioning and action of the six (or chosen number) sets or groupings of magnets, set up in adjacent opposite pole positioning (+−+−+−; ++−−++−−++−−; ++++−−−−++++−−−−++++−−−−; +(++)+−(−−)−+(++)+−(−−)−+(++)+−(−−)−; and such sets or groupings of like configurations) which facilitate the expansion and contraction, perimeter-wise, of the band 14, in its positional response to a dimensionally changing penile organ 12.

The fabric or material utilized in the construction or fabrication of the support band 14, pocketing layer subassembly 24, biasable mesh layer 24A and/or intra-magnet retainer layers 84 in preferred embodiments of the present invention described, illustrated and claimed herein; should be light in weight, easily foldable, and of enough or sufficient body and dimension to hold the magnet portions, pairings, groupings, and their encompassed individual magnet components; in place, and in functional position. A power net or mesh fabric material, when so utilized as a structural component, therein, is soft to the skin; and also allows magnet portions, groupings, or individual magnet components to be close to the skin by virtue of the mesh spacings or holes provided in such fabric material.

Examples of the TPA 10 of the present invention; as, for example, illustrated in FIGS. 1, 2, 3, 4, 5, 5A, 6, 7, 8, 9, 10, and 11; set forth six (6) attracting (adjacently, opposite−magnetic poled) sets, portions or groupings (or pairings) of individual magnet members or components, which have a preferred spacing between each other of about one-half inch (½"); i.e., each, in preferred embodiments, is spaced ½" from its adjacent set or grouping, as positioned around the circumference or perimeter of the band 14. It will be understood, in this regard, that the spacing can vary, within the scope of the invention, in accordance with the magnetic power of the individual component magnets utilized, as described in more detail herein.

The circumferential or perimetrical, dimensional magnitude of the band 14 of the present invention, by virtue of its initial starting length (for example, on a flaccid penile organ), where folded portions (described and illustrated herein) take−up part of the band's length and perimeter; is about 4.5 inches (4½"), in preferred, exemplar embodiments of the invention; and would normally be expected to be at this general perimeter dimension when installed to and interacting with a penile organ 12 in a flaccid physical state. The circumference or perimeter dimension of the band 14 expands (through puling apart of magnetic groupings and release of the band's folded areas), normally, to a perimeter dimension of about seven inches (7"), when in interaction, s described herein, with a penile organ 12 which is in a state of erection (erectile physical state). This, in general terms, would, in some positional alignments, equate, in dimensional terms, to the 'Circumference' Formula (as understood in conventional mathematics), of $C = R \times 3.14(2)$ (where R equals the radius); therein equating to a band (14) diameter of about 1.4 inches in substantially non-expanded (unexpanded) state (interacting with a flaccid penile organ), to a diameter of about 2.2 inches in an expanded state (in interaction with an erectile penile organ). These dimensions would normally be expected to accommodate such changes in penile organ size in many men. However, it will be understood that such dimensional magnitudes would vary to a lesser or greater magnitude in accordance with smaller or larger dimensioned penile organs with which the TPA 10 respectively interacts. Additionally, the relationship, or matrix, of distance between magnetic groupings or individual magnet components, and the power of the individual magnet components, could be changed, within the scope of the present invention, to give or produce different resulting perimeter dimensions and band diameters (within the scope of the invention).

The action of the six, or selected number, of magnetic portions or groupings, which attract one another adjacently (at their perimeter or circumferential, or arced ends); expand and contract the band 14 (in accordance with folded portions thereof retained or released) to adjust to the changing circumference or perimeter of the penile organ 12; while keeping the band 14, and the magnets secured thereon, snug and flush to the skin tissue of the penile organ 12, without being too tight (or any great chance in the band's perimeter pressure), during erections of the penile organ 12.

The penile organ 12 is known, physiologically, to gradually become larger; i.e., larger circumference or perimeter dimension; during an erection of the penile organ. During the erection process of the penile organ, the band 14 progressively expands, within its perimeter limitations, by virtue of the pulling apart (by virtue of the pressure exerted by the enlarging penile organ) of the otherwise attracting, individual magnetic portions 26, pairings 53 or groupings (26A or 26B). The outward pressure (perimeter-wise or circumferentially) exerted or brought to bear by the dimensional expansion of an erectile penile organ; may, in fact, be only strong enough, in certain cases, to pull two (2) or three (3) portions or groupings of magnets apart (of, for example, six such portions, pairings or groupings), while still leaving the band 14 in an adjusted position permitting the magnets to be held flush and snug around or against the penile organ 12, at a given state of erectility. As the penile organ 12 contracts, becomes smaller or loses its erectile state, the magnetic portions, pairings or groupings (26, 53, 26A or 26B) of attracting magnets, that have earlier been pulled apart, attract to one another, again, causing folded portions 66 to once again take up portions of the band's perimeter, as the magnetic groupings, etc., become proximate or re-attach to each other at adjacent portions thereof, as illustrated and described. As indicated, at the same contemporaneous time, the band 14, and any attached fabric layers, folds at folded portions 66, spatially taking up any spacing portions 68 that formerly existed between respective portions, pairings or groupings; and the band 14 is restored substantially back to its original positional state around or about a flaccid or flaccid-like penile organ, by virtue of the perimeter spacings or portions of the band 14 taken up by the folded portions 66, brought about by the attraction of the grouped magnets.

In this contracted or flaccid state of the penile organ 12, there is an almost continuous ring of magnets or magnet components around the penile organ in flush position in relation thereto. At this point, the separation between magnetic portions and groupings is defined by the folded portions 66, or folds, on the band 14, and magnet securing layers attached thereto, as illustrated and described herein.

Therefore, the selected number of magnetic portions, pairings or groupings; 26, 53, 26A or 26B (for example, six, as illustrated); of attracting magnets, by virtue of the adjacent, or serial, opposite pole placement (each, in reference to the other), facilitates the expansion and contraction of the band 14, upon which the magnets are secured, during sleep, nightly or other penile erections.

FIGS. 5, 5A, 8 and 11 illustrate, by example, preferred embodiments of the invention where the TPA 10 is responding automatically to a penile organ 12 in a flaccid or substantially flaccid state. As so illustrated, these drawing figures show the response of adjacently positioned, oppositely charged magnetic components, attracting and pulling toward each other; and, in so doing, taking up portions of the band 14 and attached layers to create folded portions 66; in response to the smaller perimeter and/or circumference of the penile organ 12. The referenced illustrations in FIGS. 5, 8 and 11, demonstrate, by illustrative example, the positional magnetic affinities and relationships illustrated in FIG. 12; and show by exemplar positional arrows 28/30 the tendency, upon reduced penile size, for magnetic components of the present invention to draw together or proximate to one another as the penile organ becomes or initially exists in a flaccid state. FIG. 5A illustrates, by example, the positional state of the TPA 10 when all such opposing magnetically charged components have drawn together, creating, automatically, the smallest perimeter sizing of the TPA 10 installed in contact and interaction with a penile organ 12.

Importantly, with respect to inclusion in the teaching of the present invention; the magnetic portions, pairings or groupings of magnets as positioned, by virtue of their respective adjacent, opposite magnetic pole placement, their magnetic power and pole-position characteristics, and their resulting consequent respective attraction, one to the other, serially or adjacently (grouping to grouping); these things augment the novelty of the invention. The nature of the a mesh-fabric constructed band 14, in preferred embodiments of the invention, or a ribbon-like material band and mesh fabric securing and positioning layer, or layers, such as the pocketing layer 24, biasable mesh 24A or intra-magnet retainer layer 84; helping to secure the various individual magnetic components and configurations thereof; also, augment the invention's functional purpose and novelty; although in a secondary role to the magnets themselves. Therefore, in regard to these novel characteristics; when the band 14 is fully expanded; utilizing its entire length or perimeter; in response and interaction to an erectile penile organ; there is, importantly, no more pressure from the band 14 upon the penile organ 12 than there is, or would be, when the band 14 is not expanded its full length, in response to a flaccid penile organ. Thus, there is a substantial equalization or standardization or uniformity of the inward or inboard perimeter or circumferential pressure against a penile organ, to and from each of its installed adjustable positions: i.e., its first position when the band 14 is substantially non-expanded (unexpanded) and taken up by the magnetically induced folded portions 66 (or folds) in response to a flaccid penile organ; and in its second position, when the band expands to its longer perimeter dimension, as the folded portions 66 are forced to flatten out (to spacing portions 68), and the opposing oppositely charged magnetic portions or groupings are pulled apart, lengthening the band perimeterically. This novel feature of the present invention overcomes prior art devices which utilized a simple stretchable fabric or bandage to adjust to installation sites, which often placed too much pressure on an area, restricting or preventing healthy blood flow, etc. Certainly, in the case of providing magnetic therapeutic treatment to tissue areas of a penile organ, such prior art devices would have placed blood-flow restricting pressure on the organ; in simply, elastically adjusting to larger perimeter sizes of an erectile penile organ 12.

Another preferred embodiment of the TPA 10 is illustrated in FIGS. 6, 7, 8, 12, and 13. In this and related embodiments of the present invention; the TPA 10 is provided with the support band 14, the pocketing layer 24 in the form of a biasable (retractable and expandable) layer.

The magnetic portion members 26 are provided in the special form, in these related preferred embodiments, of a number of magnetic groupings 26A. Each of the magnetic groupings 26A is provided with a number of individual magnet components 60. Each of the individual magnet components has the positive end 28A and the negative end 30A, similar to other embodiments of the present invention described herein. Each of the individual magnet components 60 is positioned in contacted series in relation to one another on the inboard surface 34 of the support band 14, as illustrated, in a substantially transverse (or perpendicular) positional relation to the lengthwise axis 29 of the band 14.

In these related preferred embodiments, as well, the respective magnetic groupings 26A are positioned on and secured to the band 14, so that each grouping 26a is spaced from its adjacent neighboring grouping. Also, each of the individual magnet components 60 within a magnetic grouping 26A are positioned so that their respective positive and negative ends 28A and 30A are positioned so as to be contacted and adjacent to one another. In so doing, the magnet components 60 are positioned and secured so that the magnetic grouping at either end 28A and 30A, alternates from positive to negative, or negative to positive, in substantial magnetic charge, along either widthwise perimeter 38 and 40 of the support band 14; as illustrated, by example, in FIGS. 6, 12, and 13.

The pocketing layer 24, in these embodiments, is attached to the band 14, and utilized to pocket or compartmentalize each of the magnetic groupings 26A, binding each of the number of individual magnet components 60, within a respective grouping 26A, in contact with each other, side-by-side; and also providing a dimensioned spacing or distance between each respective grouping 26A, as described and illustrated, while providing self-adjusting dimensional size capability in response to the changing size and cross-sectional dimensions of a penile organ 12.

Means, or a preselected subassembly, as earlier described for coupling the support band 14 into a continuous connection, loop, or circumferential-type configuration, is also provided in these related embodiments.

As is the case in other embodiments of the present invention, the TPA 10, in these related embodiments is installed about or around a preselected tissue location of a penile organ 12; and, by virtue of its differentially biasable band and biasable pocketing layer system, is self-adjusting to the changing cross-sectional or circumferential dimensions of a penile organ 12; physiologically or anatomically brought about on the penis of a live person or animal; while, also providing thereto a magnetic field of opposing magnetic charges, and the pushing and pulling effect of the TPA 10 on the penile organ 12 as a result of interacting magnetic charges of its magnetic groupings 26A and the attraction and repulsion thereby produced.

Figure 6:
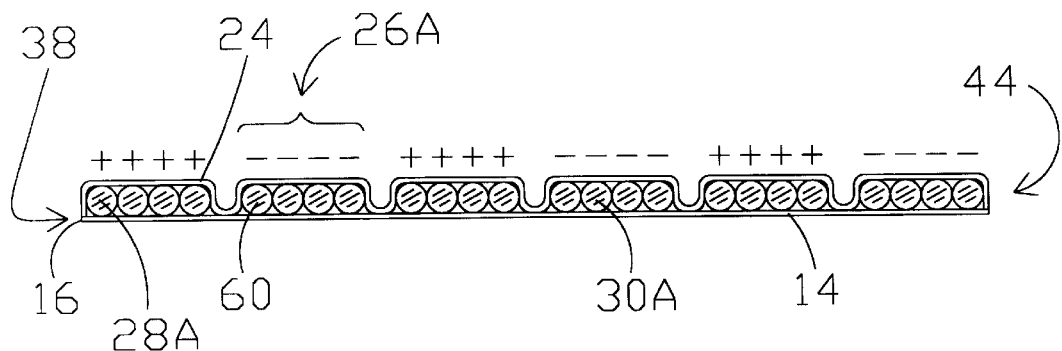
FIG. 6 is a perimeter side view of another preferred embodiment of the magnetic therapeutic penile band of the present invention.
Figure 7:
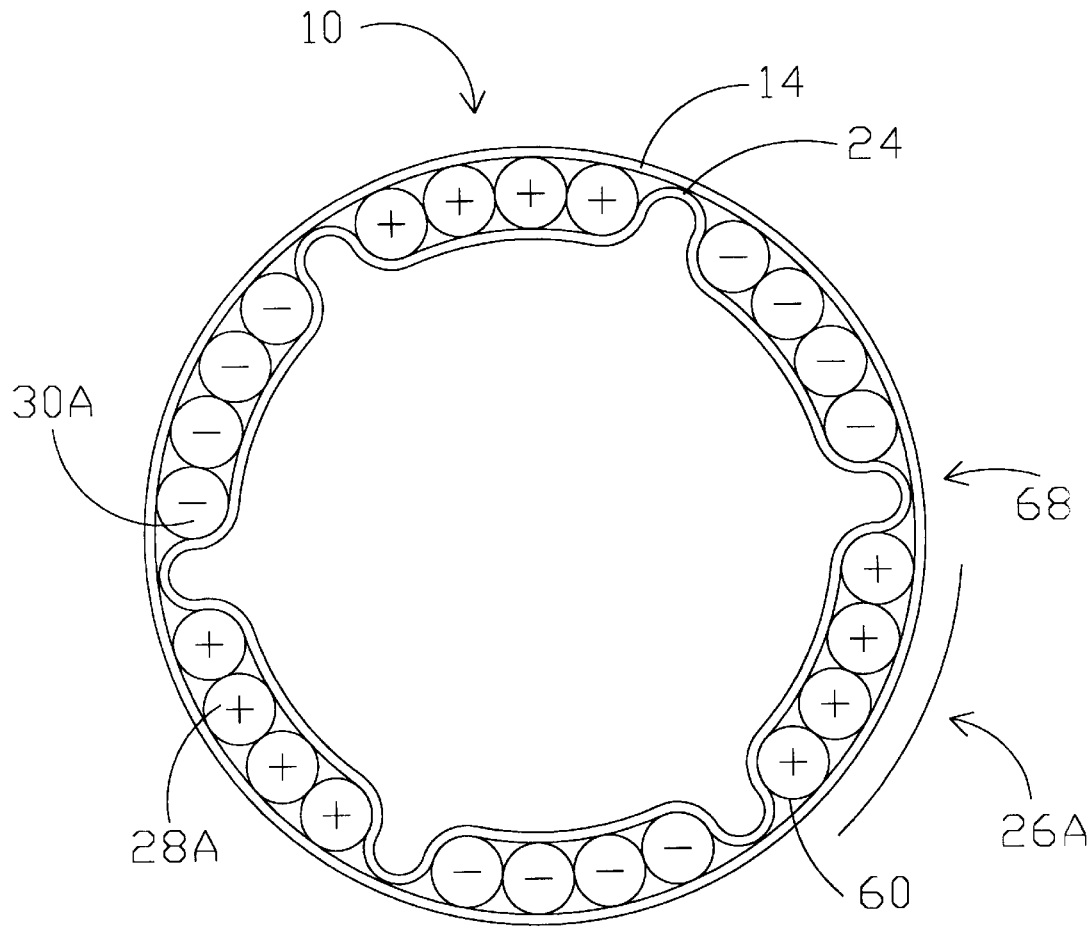
FIG. 7 is an enlarged elevated side perimeter view of the invention, of FIG. 6, in a generally enlarged and expanded positional configuration, similar to the invention's positional state when installed on a dimensionally enlarged or erectile penal organ with which the invention interacts.

In related preferred embodiments two or more magnetic groupings 26A are positioned and secured in the manner described above, between the support band 14 and the pocketing layer 24; and extend along the band 14 in a serial arrangement, between the first end 16 and the second end 18 of the band 14; as illustrated in FIGS. 6 and 7. One preferred arrangement, in this regard, is illustrated in FIGS. 6, 7 and 8; illustrating the TPA 10, as provided, by example, within the invention's scope, with six (6) magnetic groupings 26A, where each of the groupings 26A is provided with four (4) individual magnet components 60.

Examples of preferred embodiments of the TPA 10 of the present invention illustrated in FIGS. 2, 3, 4, 5, 4A, 5A, 7, 8, 10, 11, 15 and 16; set forth; teach and illustrate structural and functional advantages of the present invention which facilitate the invention's ability to self-adjustably respond in relation to the size or dimensional changes of a penile organ 12, to or from a flaccid penile organ or an erectile penile organ.

The general configuration and positional relation of the support band 14 and the pocketing layer 24 in relation and interaction with a flaccid or smaller dimensioned penile organ is illustrated by example in FIGS. 5, 5A, 8, and 11, showing a number of folded portions 66, which can also take the form of bent folds, crimped or pleated portions, or corrugated or wrinkled portions. The folded portions 66, each, comprise portions of the support band 14 and the pocketing layer 24. The general configuration and positional relation of the support band 14 and the pocketing layer 24 in relation and interaction with an erectile or larger dimensioned penile organ is illustrated by example in FIGS. 3, 7, 10, 15, and 16, showing, then, in this positional adjustment stage of the TPA 10, in the area that constituted respective folded portions 66; then, spacing portions 68 between respective magnetic portion members 26 or magnetic groupings 26A.

Figure 13:
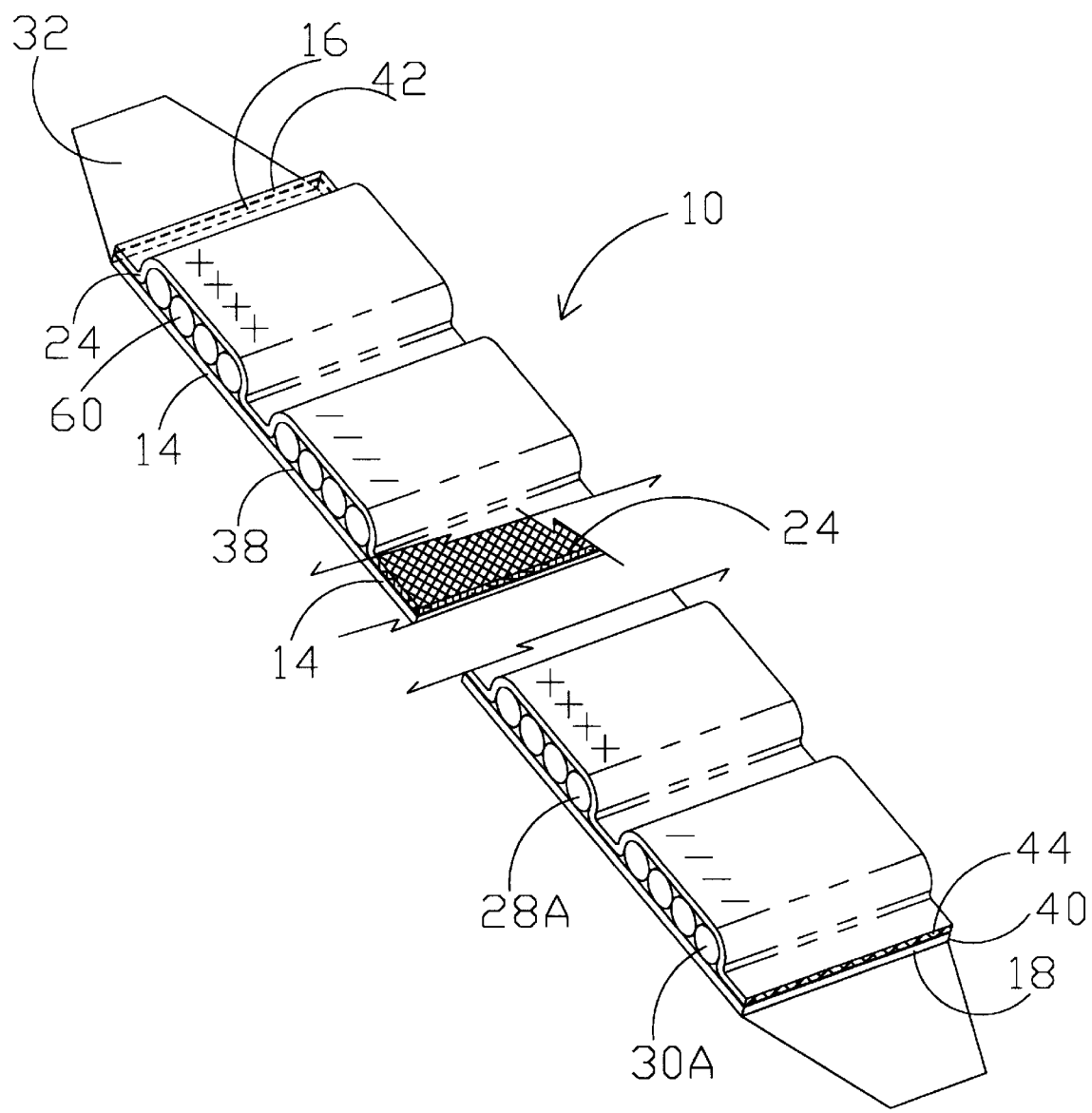
FIG. 13 is a partial perspective and cross-sectional view of another embodiment of the invention, and layers thereof, related to the embodiments of FIGS. 6, 7, and 8.
Figure 14:
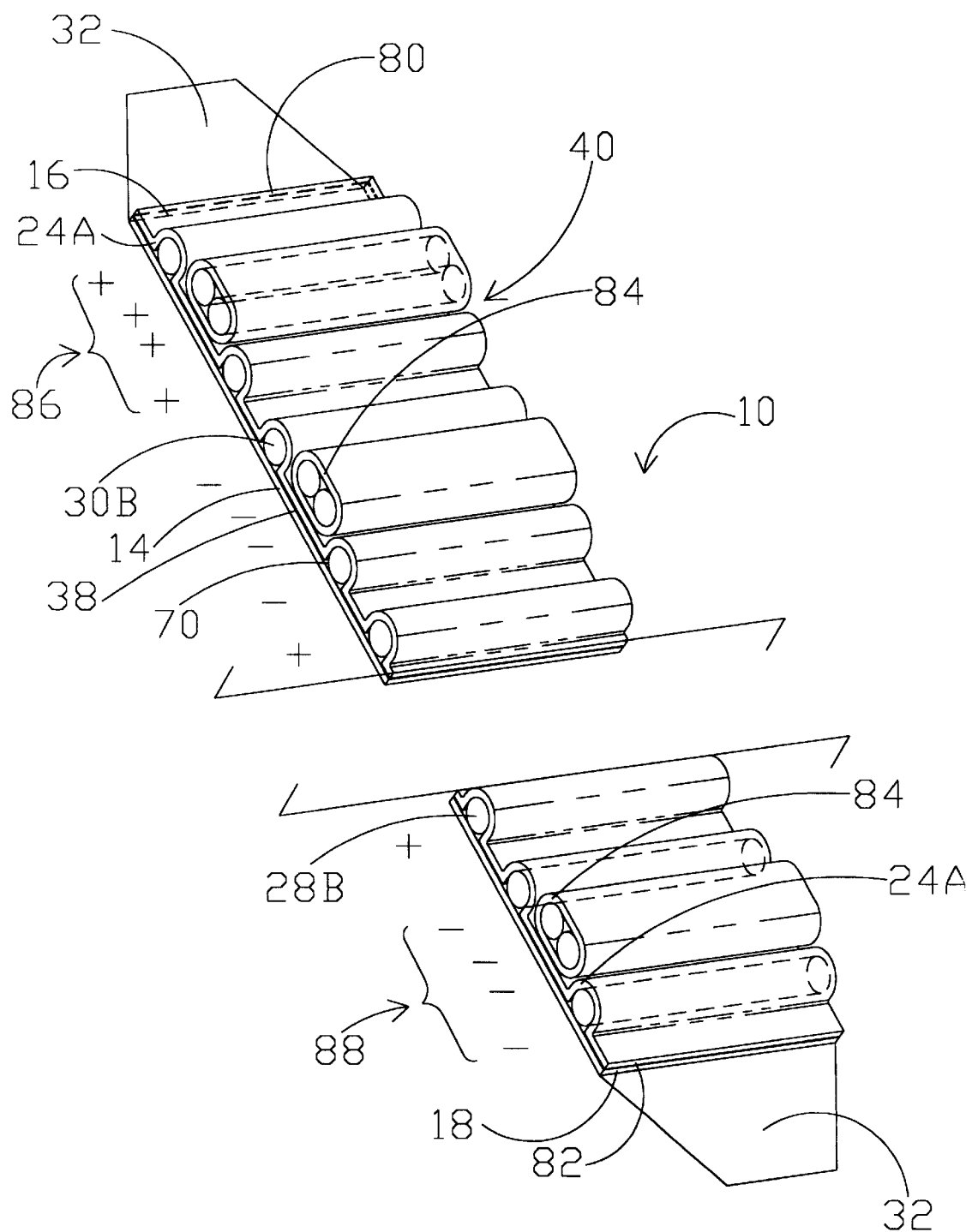
FIG. 14 is a partial perspective view of an embodiment of the present invention related to FIGS. 9, 10 and 11.

FIG. 13 illustrates, in relation to the preferred embodiments of the invention described earlier, and illustrated in FIGS. 6, 7, and 8; the differential relationship of the support band 14 having a generally partially elastic biasability characteristic of a tape or ribbon-like construction; with the pocketing layer 24 having a greater elastic biasability and being preferably constructed or a more expandable, biasable and/or retractable mesh fabric constructive material.

In another preferred embodiment of the present invention, illustrated in FIGS. 9, 10, 11, 12, and 14; the magnetic therapeutic penile band of the present invention and TPA 10 is used in biasably or snug, pressure-fitted contact and interaction with skin or tissue areas on a penile organ 12; and also in interaction and contact with changing size and dimensions of a living, penile organ 12.

As in other embodiments, the TPA 10, in these related embodiments, is provided with the support band 14 having first and second ends 16 and 18, respectively; inboard and outboard surfaces, 34 and 36; and widthwise perimeter portions, 38 and 40. The TPA 10 is provided with the plurality or number (more than one (1)) of magnetic groupings 26B, having a number magnet components 70, each of which is positioned in adjacent or proximate relation to one another, and in at least proximate or close positional relation to the inboard surface 34 of the band 14. Each of the magnetic groupings 26B is positioned on the band 14 so that each grouping 26B is spaced or a dimensioned distance from its neighboring grouping 26B; and so that each grouping 26B constitutes in relation to its neighboring spaced and adjacent grouping, an opposite magnetic charge (or magnetic field charge), in terms of substantial positive or negative magnetic charge; as illustrated, by example, in FIGS. 9, 10, 11 and 14.

Figure 9:
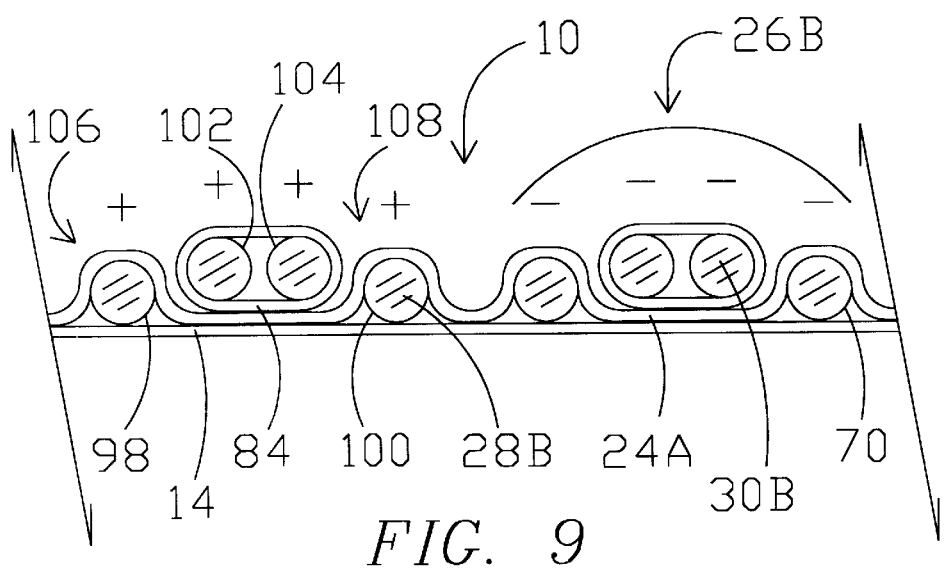
FIG. 9 is a partial side perimeter view of another preferred embodiment of the magnetic therapeutic penile band of the present invention.

Also, in these preferred embodiments, the TPA 10 is provided with the biasable mesh layer 24A with its first and second ends 80 and 82, which is attached at selected portions of the band 14 as illustrated by example in the drawings. In this manner, the present invention teaches its means or system, in these embodiments, for biasably supporting, pocketing and spacing at least two of the magnet components 70 within a given magnetic grouping 26B, or at least one component 70, at either end of such a grouping 26B, while also providing securement for part of the components 70 of the grouping 26B, and spacing between each grouping 26B; as illustrated in FIG. 9, and other referenced related drawing figures.

In these embodiments, the TPA 10 is also provided with the intra-magnet retainer layers 84, which are respectively positioned around or about at least two (2) or more magnet components 70 positioned between the components 70 retained and pocketed by the mesh layer 24A, as to each grouping 26B. In so doing, the invention thereby teaches a means, system or method for separately retaining and utilizing a number of such components 70, or one larger combined entity of two or more magnet components 70, within each magnetic grouping 26B in this embodiment, for purposes of fulfilling the functional objects of the present invention; in this manner connecting the magnet components 70, retained by the intra-magnet retainer layer 84 within each grouping 26B, by attachment of the retainer 84 to a portion of the mesh layer 24A, or the mesh layer 24A and band 14; as illustrated in FIGS. 9, 10, 11, and 14. This embodiment, as described in other embodiments herein, is also provided with coupling 32 for attachment and connection, or integral connection, of the ends 16 and 18, or ends 16, 18, 80 and 82. Each of the intra-magnet retainer layers 84 is constructed of a partially or differentially elastic or expandable, ribbon or tape-like material, similar to that of the support band 14; but can also be constructed of other biasable or supporting materials, magnetically neutral in quality.

In related preferred embodiments to those just previously described, illustrated and claimed herein; the number of magnetic groupings 26B provided includes first, second, third, fourth, fifth and sixth magnetic groupings; respectively, 86, 88, 90, 92, 94, and 96; illustrated by example in FIGS. 10 and 11. Therein, as illustrated in FIG. 9, each of these groupings, 86 through 96; is provided with four (4) magnet components 70. The first individual magnet component 98 is positioned on the band 14 at the first end magnet position 106 of each grouping 26B, and the second individual magnet component 100 is positioned on the band 14 at the second end magnet position 108 of the respective grouping 26B.

The first and second individual magnet components 98 and 100 are secured, pocketed, and spaced or distanced form one another, in their secured position, by the biasable mesh layer 24A. The third and fourth individual magnet components 102 and 104 are positioned contacted, adjacent or proximate, serially, to one another, on the biasable mesh layer 24A; between the first and second individual magnet components 98 and 100 secured by the layer 24A; and these magnet components 102 and 104 are compartmentalized, pouched or pocketed together by one of the intra-magnet retainer layers 84, which securably wraps around or about magnets 102 and 104 and secures them to the biasable layer 24A, or to the layer 24A and the support band 14.

Figure 15:
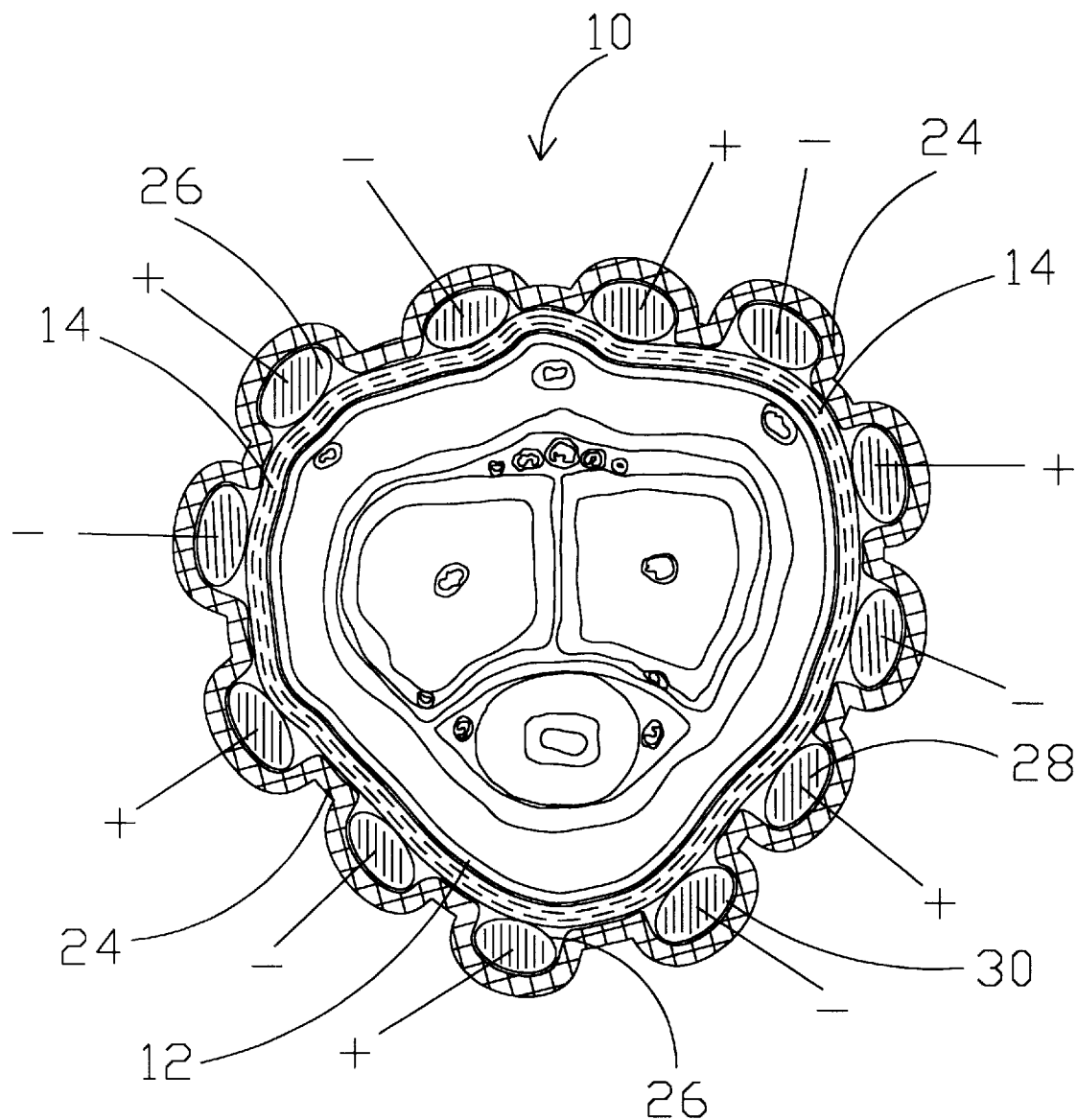
FIG. 15 is a cross-sectional view of another embodiment of the present invention, illustrating the cross-sectional anatomy of a human penile organ in general diagrammatic atlas form, symbolizing an exemplar penile organ with which the present invention interacts.
Figure 16:
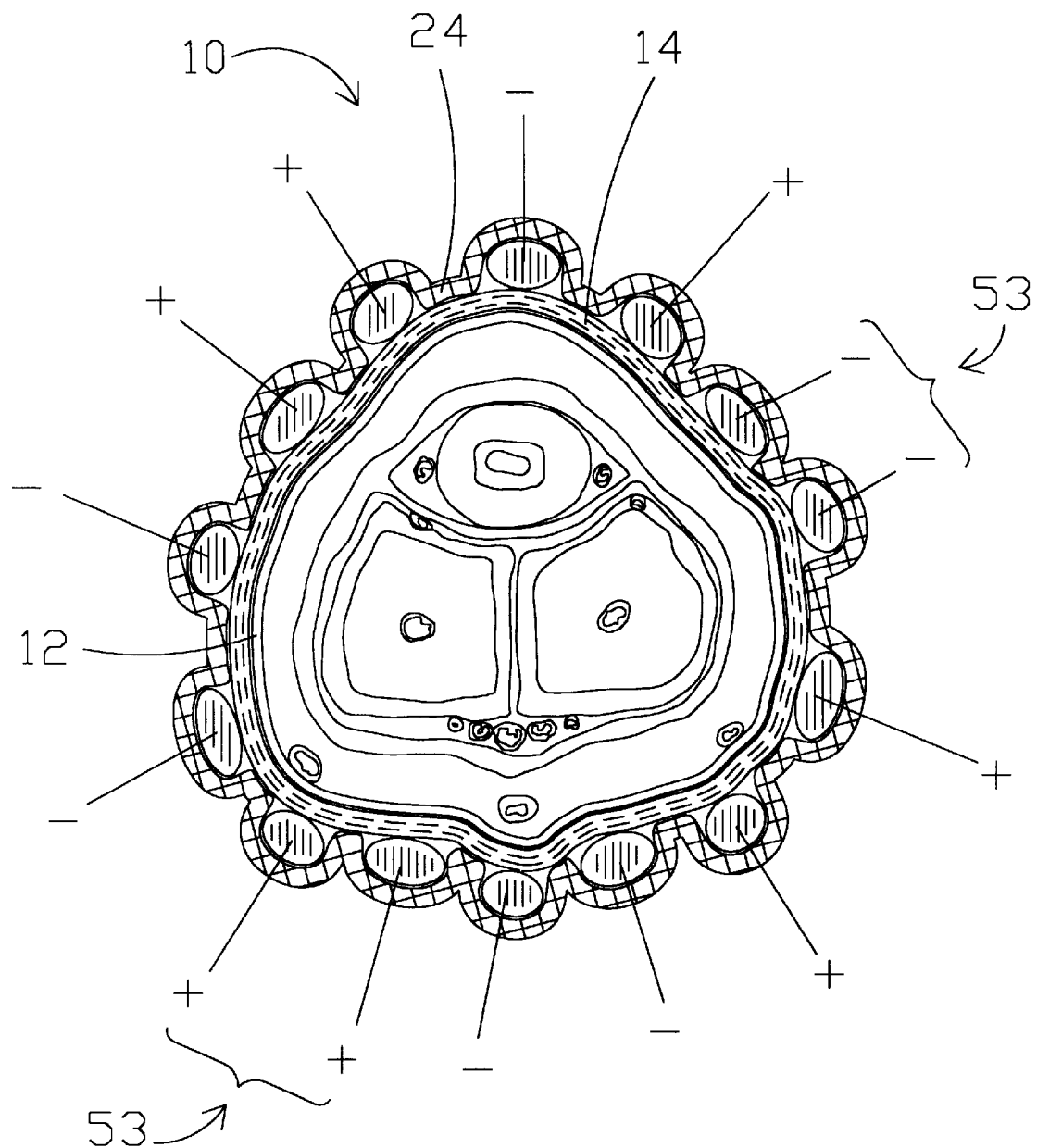
FIG. 16 is a cross-sectional view of another embodiment of the present invention, illustrating the cross-sectional anatomy of a human penile organ, in general diagrammatic atlas form, symbolizing an exemplar penile organ with which the present invention interacts.

As illustrated in FIGS. 15 and 16, various embodiments of the present invention, within the scope and spirit thereof, are provided, utilizing corrugated, pocketed magnetic members or components, and intervening spacing therebetween, to employ individual magnetic charges at the ends of such magnets in relation to one another, or adjacent or serial groupings of a plural number of similar magnetic charges, constituting together a substantially positive grouping of charges or a substantially negative grouping charges; and, in each case, varying the magnetic charges so that they are substantially opposite in neighboring positional relation to one another, as illustrated by example, in the drawings.

As also illustrated in FIGS. 15 and 16, the TPA 10 of the present invention; surrounds, or is installed about, a turgid, larger or erectile penile organ 12; and in such contacted interaction is able to exert, or bring to bear, a movement of the band 14 and layer 24, and equivalent members in its related additional embodiments described herein, to adjust to different sizes or dimensions of the organ 12; to produce, at least to some extent a physical movement or massaging effect upon the organ 12; and exert a magnetic field of contributing positive and negative magnetic or electrical charges, and attracting and repulsing magnetic action, to provide a therapeutic effect to areas or tissue of the penile organ 12; including, the Skin, the subcutaneous tissue, the Superficial Dorsal vein, the Dorsal artery and nerve, the Lateral Superficial vein, the Superficial (dartos) fascia, the Deep (Buck's) fascia, the Deep Dorsal vein, the Corpus cavernosum, its Tunica Albuginia (erectile tissue) and the Deep artery therein; the Intercavernous septum of Buck's fascia, the Corpus Spongiosum and its tunica albuginea, and the Uretha; or part of these tissues or anatomical parts; all of which are illustrated by example generally by anatomical sectional drawing in FIGS. 15 and 16, with interacting symbolic magnetic charges indicated therein.

It will be understood that the basic theory of attraction of different magnetic charges ("+" vs. "−") and repulsion (or movement away) of like magnetic charges ("+" vs. "+" or "−" vs. "−") is present and forms significant functional workings in the present invention, to facilitate the magnetic or differential magnetic field, the self-adjusting function (along with differentially elastic support and pocketing layers), and the related physical movement of the TPA 10 in interaction and relation to the penile organ 12.

Figure 12:
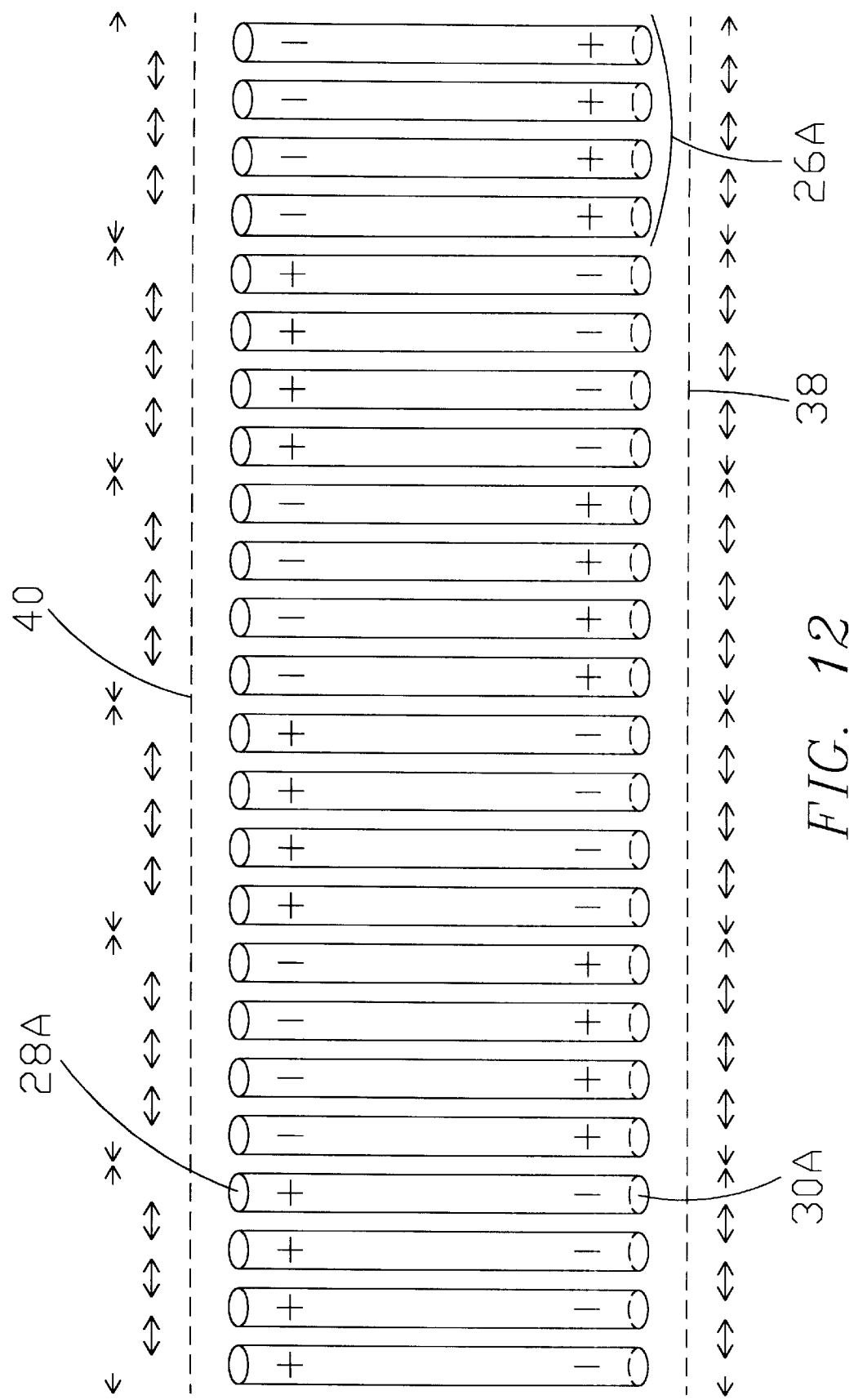
FIG. 12 is a diagrammatic illustration of the general polar magnetic forces, and directional fluxes, at work, illustrated by symbolic arrows, in the present invention, of FIGS. 6, 7, 8, 9, 10 and 11; and, theoretically, in the other embodiments of the present invention.

In this regard, various directional magnetic forces are illustrated schematically by example in FIGS. 12, as to embodiments of the present invention set forth in FIGS. 6, 7, 8, 9, 10, 11, 13, and 14; and the basic magnetic and directional principles set forth therein, apply to the other related embodiments of the present invention; and to other modifications and examples of the present invention with its full scope and spirit.

Also, as shown in the embodiments of the present invention set forth and illustrated in FIGS. 15 and 16; the band 14 and the pocketing layer 24 can be inverted so that the band 14 is inboard and closest to the tissue of the penile organ 12, and the layer 24 is outboard or positionally outside the band 14, as illustrated. In such embodiments, the band 14 and the layer 24 are fabricated of similar elastic mesh fabric, or can be constructed of various materials earlier discussed herein, neutral or user-friendly in interaction with magnetic elements and components of the invention.

Such constructive materials as to the band 14, the layer 24 and the magnetic portion members 26 (and other magnetic component embodiments previously discussed herein) can each, in relation to one another, be fabricated of materials having differentially varying (or different) elastic qualities, dynamics and/or stretch or size-changing characteristics, as to their ability to contract and expand; or may be of like or similar makeup in this regard. Also, magnets or magnetic components of circular, elliptical or cam-shaped (or cam-like) cross-sectional configuration, or magnets of other shapes or configurations; can be utilized as part of the magnetic portion members 26, and its other related preferred embodiments set forth herein as the magnetic groupings 26A, the individual magnet components 60 (of 26A), the magnetic groupings 26B, the magnet components 70 (of 26B); and the spaced pairings of magnets 53; described, illustrated and claimed herein; each within the scope and spirit of the present invention.

Additionally, different strengths, sizes and magnetic constructive material can be utilized within the scope of the invention.

The term, "therapeutic," as utilized herein, denotes that which serves to cure or heal; that which is curative; that which server to preserve or restore health; that which treats disease or any physical disorder by medical or physical means, or the treatment or cure of such disorders; and/or the science or art of healing. The curative powers of magnetic principals, through various means, distinguishable from the present invention, has been known and practiced in the therapeutic/medical arts; and the disease or medical and physical disorder of vascular disease, erectile dysfunction and/or problems associated with lack of proper blood flow have been problems recognized to exist in human and animal patients; and in the nature of such disorders that have been addressed through therapeutic means.

The coupling subassembly 32 in preferred embodiments of the invention is in the form of inter-fitting or coupling subportions, for securely interfacing, linking and/or coupling ends 16 and 18. Additionally, as indicated above, herein, in preferred embodiments, the coupling subassembly is provided in integral construction, connecting and interfacing ends 16 and 18.

A group of preferred magnetic components for use in the present invention, although others, or equivalents to those listed here, are utilizable, includes magnets having the following characteristics and dimensions:

THICKNESS OF MAGNET (OR DIAMETER): about 0.12 inches; or a range of from about 0.05 inches to about 0.15 inches LENGTH OF MAGNET: about 0.625 inches; or a range of from about 0.40 inches to about 1.0 inch TYPE OF MAGNET: "Alnico"®

POWER OF MAGNET: about 5; or a range of from from about 3 power to about 7 power DISTANCE APART: (Individual Magnetic between individual magnetic Components) about ¼ inch (¼") components or magnets within a magnetic portion 26, pairing 53, or grouping 26A, 26B, or 26C; or a greater or lesser dimensional distance in accordance with Note I*

DISTANCE APART: (BETWEEN MAGNETIC PORTION, PAIRING OR GROUPING) about ½ inch (½" or 0.50"); or a greater or lesser dimensional distance in accordance with Note I*

Note I*: Greater individual magnet power permits greater dimensional distance apart, where less magnetic power requires a closer dimensional distance apart.

HOW MAGNETIZED: By ends, one lengthwise end being substantially a North pole, the other end substantially a South pole, as to magnetic field charge CONFIGURATION: generally, cylindrical in shape with first and second lengthwise ends (two such ends)

Figure 18:
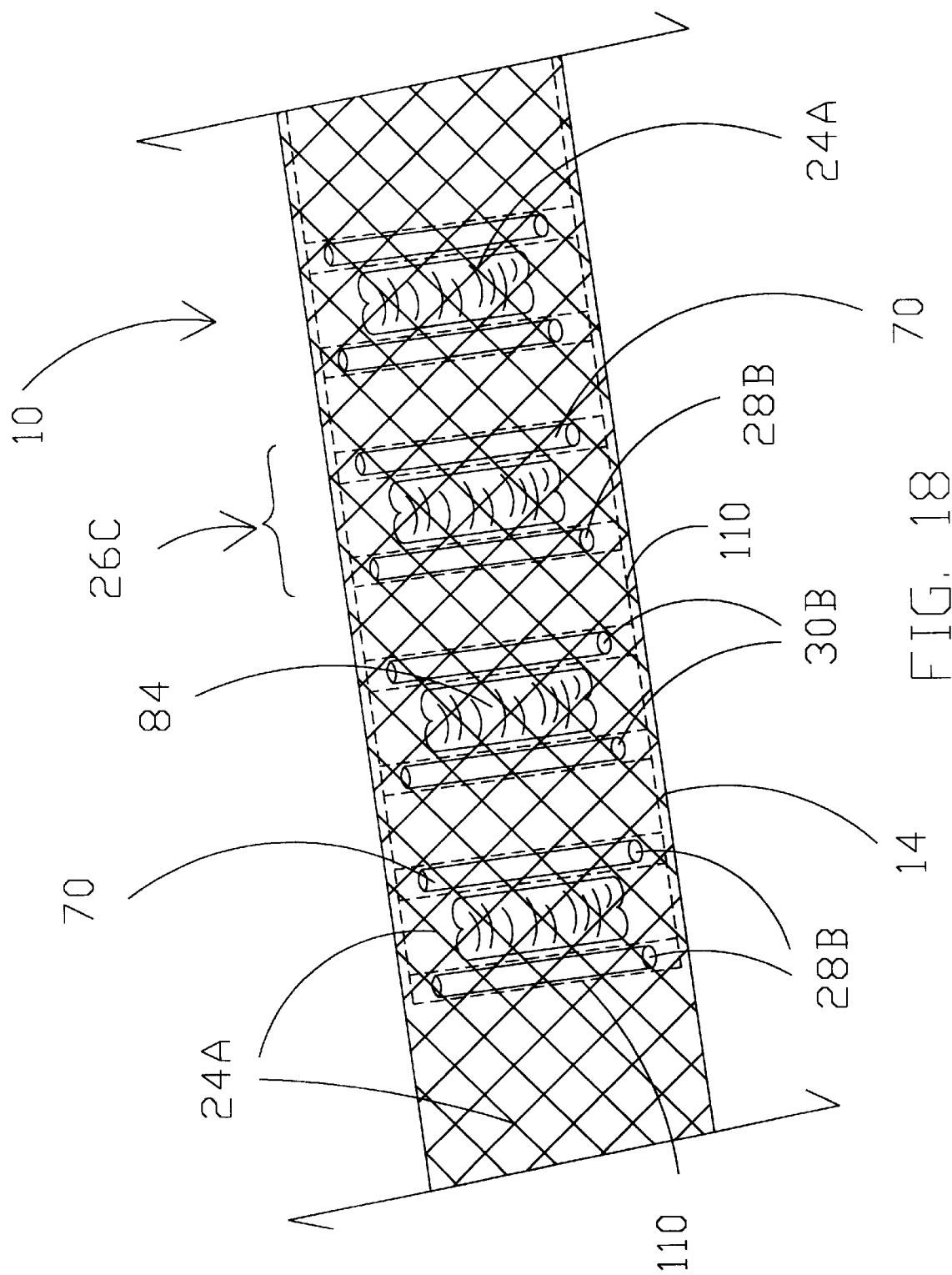
FIG. 18 is a partial elevated perspective view of another embodiment of the present invention.
Figure 19:
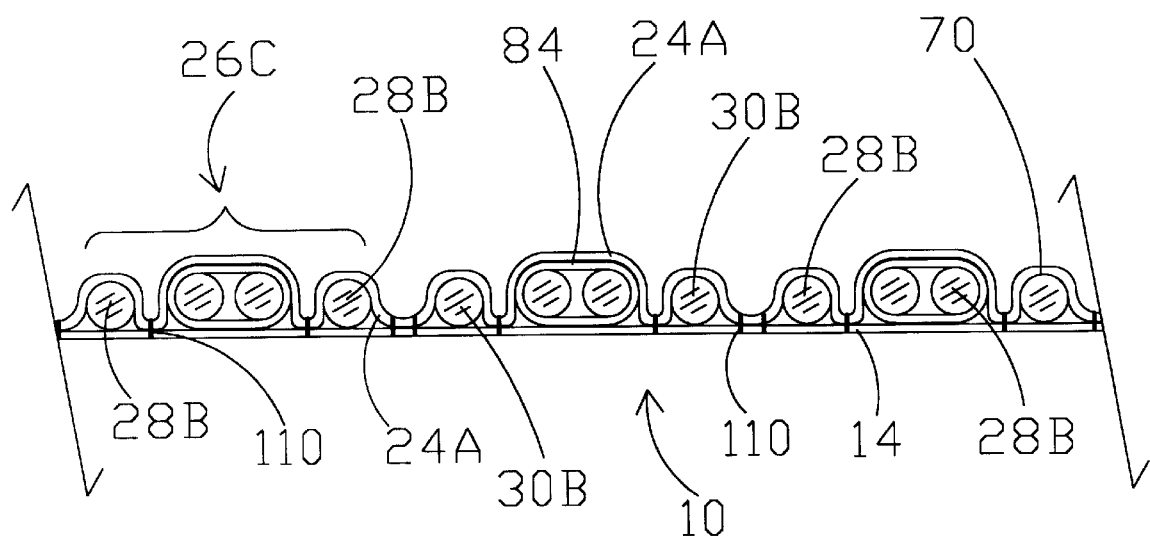
FIG. 19 is a partial side perspective view of the embodiment of the invention of FIG. 18.

An additional, related preferred embodiment of the present invention is taught by the invention; similar to that illustrated in FIGS. 9 through 12, and 14. This preferred embodiment is illustrated in FIGS. 18 and 19. In this embodiment, or related such embodiments, of the invention, the TPA 10 is provided with many elements previously disclosed, claimed and illustrated herein. The mesh layer 24A, however, in this embodiment is utilized to contain and secure each of the magnet components within each respective magnetic grouping 26C of this embodiment against the band 14 by virtue of securing means 110; which, in one preferred form is stitching, or threading fabrication, as illustrated by example in FIGS. 18 and 19. Other means such as cementing, integral construction and other attachment construction can also be utilized as the securing means 110 to secure, and hold in position, all of the components 70 and each of the groupings 26C. Similar to the deployment and patterning of components 70 described in the previous embodiment just above herein (re FIGS. (9–12, & 14), each of two components 70 is positioned and secured individually at either end of each grouping 26C, and two of the components are secured together in the middle portion area between these end components 70 at either end. These middle components 70 are separately wrapped or contained in a separate intra-magnet retainer 84. The middle portion area magnets, so contained by the respective retainer 84, are, themselves, covered, further secured and held in position against the band 14 by the mesh layer 24A and securing means 110; forming a separate secured pocket for each of the middle portion area magnets of each of the groupings 26C utilized. In this manner, three separate stitched or secured pockets, by virtue of the mesh 24A and the securing means 110, are created for each grouping 26C secured between the mesh 24A and the band 14; as illustrated by example in FIGS. 18 and 19; and all of the magnet components 70 utilized in this patterning of this preferred embodiment are covered by the mesh 24A.

Accordingly, the appended claims are intended to cover all changes, modifications and alternative options and embodiments falling within the true breath, scope and spirit of the present invention. The reader is, therefore, requested to determine the scope of the invention by the appended claims and their legal equivalents, and not by the examples which have been given.

I claim:

1. A self-adjusting therapeutic penile band assembly, for use, when installed, in flexibly contacted interaction with a mammal penis, during cross-sectional dimensional changes thereof, for contemporaneously providing a magnetic field, when in an installed position on a mammal penis, to adjacent areas thereabout to improve the flow of blood circulation and physiological function thereof, said self-adjusting therapeutic penile band assembly comprising:

a support band having first and second ends and a longitudinal-lengthwise axis therebetween, inboard and outboard surfaces, and first and second widthwise perimeter portions;

a plurality of magnet members, each respective magnet member having a first end, substantially positive in magnetic charge, and a second end, substantially negative in magnetic charge, each generally positioned along a lengthwise axis of the respective magnet member, eaqch of said respective magnet members being positioned in adjacent series on the inboard surface of the support band such that its lengthwise axis is substantially parallel with, and spaced from, that of each adjacent magnet member, and substantially transverse to the longitudinal lengthwise axis of the support band;

the support band being differentially layered, and further comprising a biasable matrix layer having first and second ends, being attached to the support band, having means for contracting and expanding, when in installed position, in relation to a cross-sectional size and dimension of a mammal penis, and means for biasably supporting and pocketing each of said plurality of magnet members in adjacent positional relation to, and against, the inboard surface of the support band; and means for coupling the respective first ends of the support band and the biasable matrix layer in adjacent positional relation to the respective second ends thereof.

2. The self-adjusting therapeutic penile band assembly of claim 1,
   wherein:
      the support band is fabricated from a flexible, foldable and bendable constructive material in the general configuration of a strip, the support band being fabricated from a group of construction materials, including ribbon assembly material, tape material, elastic polymer materials and resilient, flexibly biasable substances.

3. The self-adjusting therapeutic penile band assembly of claim 2,
   wherein:
      said means for coupling, said support band and said biasable matrix layer are integral in construction.

4. The self-adjusting therapeutic penile band assembly of claim 2,
   wherein:
      said means for coupling is fabricated of a hook and loop construction.

5. The self-adjusting therapeutic penile band assembly of claim 2,
   wherein:
      said biasable matrix layer further comprising inboard and outboard surfaces, and
      being fabricated from a contractable and expandable mesh fabric material, constructed to interface dimensionally with the support band.

6. The self-adjusting therapeutic penile band assembly of claim 5,
   wherein:
      said biasable matrix layer is attached to said support band such that the inboard surface of the support band, along its longitudinal-lengthwise axis, opposes, and is positionally adjacent to, the outboard surface of the biasable matrix layer.

7. The self-adjusting therapeutic penile band assembly of claim 5,
   wherein:
      the plurality of magnet members comprising:
         a first magnet member being positioned on the support band and individually pocketed by the biasable matrix layer such that the second end thereof is positioned generally adjacent to the first widthwise perimeter portion of the support band, and its lengthwise axis thereof is generally adjacent to the first end of the support band;
         a second magnet member being positioned on the support band and individually pocketed by the biasable matrix layer such that the second end thereof is generally adjacent to the first widthwise perimeter portion of the support band, and its lengthwise axis thereof is generally facing and adjacent to the second end of the support band and generally parallel to that of the first magnet member; and
         first and further spaced pairings of magnet members being positioned in series between the first magnet member and the second magnet member,
         each of the magnet members of the first spaced pairing of magnet members being positioned in series on the support band, and spaced and individually pocketed by the biasable matrix layer, such that the first end of each magnet member thereof is generally adjacent to the first widthwise perimeter portion of the support band, and its lengthwise axis thereof is parallel to that of the first magnet member, and each of the magnet members of the further spaced pairings of magnet members being positioned in series on the support band, and spaced and individually pocketed by the biasable matrix layer, such that each two magnet members in series are positioned with the same end generally adjacent to the first widthwise perimeter portion of the support band, and such that each two magnet members in series, between the first spaced pairing of magnet members and the second magnet member, are oppositely positioned with regard to their respective first ends in relation to those of other adjacently positioned further spaced pairings of magnet members.

8. The self-adjusting therapeutic penile band assembly of claim 7, wherein:

the further spaced pairings of magnet members comprise:

second, third, fourth and fifth spaced pairings of magnet members, the second spaced pairing of magnet members comprising two magnet members, each being positioned on the support band spaced from one another and individually pocketed by the biasable matrix layer, and further being so positioned such that their respective second ends are each adjacent to the first widthwise perimeter portion of the support band and their respective lengthwise axes are generally parallel to each other and to the respective lengthwise axis of each of the magnet members of the first spaced pairing of magnet members, the third spaced pairing of magnet members comprising two magnet members, each being positioned on the support band spaced from one another and individually pocketed by the biasable matrix layer, and further being so positioned such that their respective first ends are each adjacent to the first widthwise perimeter portion of the support band and their respective lengthwise axes are generally parallel to each other and to the respective lengthwise axes of each of the magnet members of the second spaced pairing of magnet members, the fourth spaced pairing of magnetic members comprising two magnet members, each being positioned on the support band spaced from one another and individually pocketed by the biasable matrix layer, and further being so positioned such that their respective second ends are each adjacent to the first widthwise perimeter of the support band and their respective lengthwise axes are generally parallel to each other and to the respective lengthwise axes of each of the magnet members of the third spaced pairing of magnet members, and the fifth spaced pairing of magnetic members comprising two magnet members, each being positioned on the support band spaced from one another and individually pocketed by the biasable matrix layer, and further so positioned such that their respective first ends are each adjacent to the first widthwise perimeter of the support band and their respective lengthwise axes are generally parallel to each other and to the respective lengthwise axes of each of the magnet members of the fourth spaced pairing of magnet members.

9. The self-adjusting therapeutic penile band assembly of claim 8, wherein:

each respective magnet member of said plurality of magnet members is fabricated and constructed such that it is generally cylindrical in configuration, each respective magnet member further comprising a collar member, being positioned over its first and second ends.

10. The self-adjusting therapeutic penile band assembly of claim 5, wherein:

the plurality of magnet members comprises a plurality of magnetic groupings, each having a plurality of individual group magnets, positioned together in series, such that their respective first and second ends are adjacent to one another; and wherein each of the magnetic groups are positioned in series in reference to one another so that they constitute different magnetic charges when viewed in adjacent positional relationship to one another.

11. A self-adjusting and differentially layered magnetic therapeutic penile band, for use, when installed, in biasably contacted interaction with a preselected area of tissue, and the changing cross-sectional dimensions, of a penile organ, said self-adjusting and differentially layered magnetic therapeutic penile band comprising:

a support band, fabricated from a resilient and, at least partially, elastic substance, having first and second ends and a lengthwise axis therebetween, inboar and outboard surface areas, and first and second perimeter portions;

a plurality of magnetic groupings, each having a number of individual magnet components, each of said individual magnet components having a positive and, substantially positive in magnetic charge, and a negative end, substantially negative in magnetic charge, positioned generally along an axial spacing in relation to one antoerh, each of the individual magnet components being positioned in contacted series with one another on the inboard surface of the support band, in generally transverse positional orientation in relation to its lengthwise axis, and further being positioned such that each of the magnetic groupings is spaced from one another and constitute in relation to one another opposite magnetic charges;

said support band being differentially layered and further comprising a biasable layer having first and second ends, being fitably attached to the support band, having means for contacting and expanding, when in installed position, in relation to a cross-sectional size and dimension of a penile organ, and means for biasably supporting and pocketing each of the plurality of magnetic groupings and providing spacing therebetween, in adjacent positional relation to, and against, the inboard surface of the support band; and means for coupling the first end of the support band in adjacent positional relation to the second end of the support band, when the self-adjusting and differentially layered magnetic therapeutic penile band is installed in contacted interaction about a penile organ.

12. The self-adjusting and differentially layered magnetic therapeutic penile band of claim 11, wherein:
said means for coupling comprises an integral construction.

13. The self-adjusting and differentially layered magnetic therapeutic penile band of claim 11,
wherein:
said means for coupling comprises a hook and loop construction.

14. The self-adjusting and differentially layered magnetic therapeutic penile band of claim 11,
wherein:
said biasable layer further comprising inboard and outboard surfaces, and
being fabricated from a contractable and expandable mesh fabric material, constructed to interface dimensionally with the support band.

15. The self-adjusting and differentially layered magnetic therapeutic penile band of claim 14,
wherein:
said biasable layer is attached to said support band such that the inboard surface area of the support band opposes, and is positionally adjacent to, and contacted with, the outboard surface area of the biasable layer.

16. The self-adjusting and differentially layered magnetic therapeutic penile band of claim 15,
wherein:
the plurality of mangentic groupings comprise:
a first magnetic grouping being positioned on the support band and individually pocketed by the biasable layer such that each respective positive end of each respective number of individual magnet components is positioned generally adjacent to the first widthwise perimeter portion of the support band, in contacted series therealong, said first magnetic grouping being, in positional relation to the other respective plurality of magnetic groupings, closest and most adjacent to the first end of the support band;
a second magnetic grouping being positioned on the support band and individually pocketed by the biasable layer such that each respective negative end of each respective number of individual magnet components is positioned generally adjacent to the first widthwise perimeter portion of the support band, in contacted series therealong, said second magnetic grouping being in positional relation to the other respective plurality of magnetic groupings, closest and most adjacent to the second end of the support band; and
third and further respective magnetic grouping being positioned in series between the first magnetic grouping and the second magnetic grouping,
the third respective magnetic grouping being positioned on the support band, and pocketed by the biasable layer, such that the negative end of each respective number of individual magnet components is positioned generally adjacent to the first widthwise perimeter portion of the support band, in contacted series therealong, and said third respective magnetic grouping is spaced from, and in serial position to, the first magnetic grouping, and
said further respective magnetic groupings, each, being serially positioned on the support band, and spaced and individually pocketed by the biasable layer, such that each respective number of individual magnet components of each further respective magnetic groupings is positioned with the same end generally, positionally adjacent to the first widthwise perimeter portion of the support band, and such that each further respective magnetic groupings in series, between the third respective magnetic pairing and the second magnetic grouping, has its number of individual magnet components each positioned to produce an opposite magnetic field charge in relation to those of other adjacently spaced further magnetic groupings.

17. The self-adjusting and differentially layered magnetic therapeutic penile band of claim 16,
wherein:
the first magnetic grouping further comprising first, second, third and fourth individual magnet components, each being positioned in serial contact with one another along their respective axial spacing;
the second magnetic grouping further comprising first, second, third and fourth individual magnet components, each being positioned in serial contact with one another along their respective axial spacing;
the third respective magnetic grouping further comprising first, second, third and fourth individual magnet components, each being positioned in serial contact with one another along their respective axial spacing, the first individual magnet component of said third respective magnetic grouping being positioned serially adjacent to, and spaced from, the fourth individual magnet component of said first magnetic grouping;
the further respective magnetic groupings further comprise fourth, fifth and sixth respective magnetic groupings, in relation to the plurality of magnetic groupings as a whole,
the fourth respective magnetic grouping comprising first, second, third and fourth individual magnet components, each being positioned in serial contact with one another along their respective axial spacing, and each being positioned such that their respective positive ends are positionally, generally adjacent to the first widthwise perimeter portion of the support band, the first individual magnet component of said fourth respective magnetic grouping being positioned serially adjacent to, and spaced from, the fourth individual magnet component of said third respective magnetic grouping,
the firth respective magnetic grouping comprising first, second, third and fourth individual magnet components, each being positioned in serial contact with one another along their respective axial spacing, and each being positioned such that their respective negative ends are positionally, generally adjacent to the first widthwise perimeter portion of the support band, the first individual magnet component of said fifth respective magnetic pairing being positioned serially adjacent to, and spaced from, the fourth individual magnet component of said fourth respective magnetic grouping; and
the sixth respective magnetic grouping comprising first, second, third and fourth individual magnet components, each being positioned in serial contact with one another along their respective axial spacing, and each being positioned such that their respective positive ends are positionally, generally adjacent to the first widthwise perimeter portion of the support band, the first individual magnet component of said sixth respective magnetic grouping being positioned serially adjacent to, and spaced from, the fourth individual magnet component of said fifth respective magnetic grouping, and the fourth individual magnet component of the sixth magnetic grouping being positioned serially adjacent to, and spaced form, the first individual magnet component of said second magnetic grouping; and wherein each of the individual magnet components of each of the respective magnetic grouping further comprises a sheath member covering, at least in part, its respective positive and negative ends.

18. A self-adjusting and differentially layered magnetic therapeutic penile band for use in biasably contacted interaction with areas on and changing dimensions of a penile organ, said self-adjusting and differentially layered magnetic therapeutic penile band comprising:

a support band having first and second ends, inboard and outboard surface areas, and first and second perimeter portions;

a plurality of magnetic groupings, each having a number of individual magnet components, each of said individual magnet components having a positive end, substantially positive in magnetic field charge, a negative end, substantially negative in magnetic field charge, and a lateral portion separating the positive and negative ends in general axial orientation to one another, and being positioned adjacently in relation to one another, and in proximate positional relation to the inboard surface area of the support band, and further being positioned so that each of the magnetic groupings is spaced from one another and constitute in relation to one another opposite magnetic field charges;

said support band being differentially layered and further comprising a biasable layer having first and second ends, being fitably attached to the support band, having means for biasably supporting, pocketing and spacing at least two of the number of individual magnet components of each of said plurality of magnetic groupings onto the support band, and providing spacing between each of the plurality of magnetic groupings thereon;

a plurality of intra-magnet retainer layers, each being positioned about at least two of the number of individual magnet components of each of said plurality of magnetic groupings, and each having means for retaining the individual magnet components within their respective plurality of magnetic groupings and attaching to the biasable layer; and means for coupling the first end of the support band in adjacent positional relation to the second end of the support band, when the self-adjusting and differentially layered magnetic therapeutic penile band is installed in contacted interaction about a penile organ.

19. The self-adjusting and differentially layered magnetic therapeutic penile band of claim 18,
wherein:
said means for coupling is integral in construction.

20. The self-adjusting and differentially layered magnetic therapeutic penile band of claim 20,
wherein:
said biasable layer further comprises inboard and outboard surfaces, and is attached to said support band such that the inboard surface area of the support band opposes, and is positionally adjacent to, and contacted with, the outboard surface of the biasable layer; and wherein:
the plurality of magnetic groupings comprise:
first, second, third, fourth, fifth and sixth respective magnetic groupings, spaced from one another, each of the respective magnetic groupings having a first end magnet position and a second end magnet position, and having first and second individual magnet components, one of which is positioned on the support band at the first end magnet position and the other so positioned at the second end magnet position, the first individual magnet component and the second individual magnetic component being supportably pocketed and spaced on the support band by the biasable layer, each of the magnetic groupings further having third and fourth individual magnet components positioned on the biasable layer between the first and second individual magnet components, the third and fourth individual magnet components being contacted with one another and separately pocketed together by one of said plurality of intra-magnet retainer layers, the intra-magnet retainer layer wrapping around the third and fourth individual magnet components and securing them to the biasable layer, the first, second, third and fourth individual magnet components of the first respective magnetic grouping, each, being positioned such that their respective positive ends are positionally adjacent to the first perimeter portion of the support band, the first respective magnetic grouping being further positioned in relation to the support band such that its first end magnet position is proximate to the first end of the support band, the first, second, third and fourth individual magnet components of the second respective magnetic grouping, each, being positioned such that their respective negative ends are positionally adjacent to the first perimeter portion of the support band, the second respective magnetic grouping being further positioned in relation to the support band such that its second end magnet position is proximate to the second end of the support band, the first, second, third and fourth individual magnet components of the third respective magnetic grouping, each, being positioned such that their respective negative ends are positionally adjacent to the first perimeter portion of the support band, the third respective magnetic grouping being further positioned in relation to the support band such that its first end magnet position is serially spaced and proximate to the second end magnet position of the first respective magnetic grouping, the first, second, third and fourth individual magnet components of the fourth respective magnetic grouping, each, being positioned such that their respective positive ends are positionally adjacent to the first perimeter portion of the support band, the fourth respective magnetic grouping being further positioned in relation to the support band such that its first end magnet position is serially spaced and proximate to the second end magnet position of the third respective magnetic grouping, the first, second, third and fourth individual magnet components of the fifth respective magnetic grouping, each, being positioned such that their respective negative ends are positionally adjacent to the first perimeter portion of the support band, the fifth respective magnetic grouping being further positioned in relation to the support band such that its first end magnet position is serially spaced and proximate to the second end magnet position of the fourth respective magnetic grouping, the first, second, third and fourth individual magnet components of the sixth respective magnetic grouping, each, being positioned such that their respective positive ends are positionally adjacent to the first perimeter portion of the support band, the sixth respective magnetic grouping being further positioned in relation to the support band such that its first end magnet position is serially spaced and proximate to the second end magnet position of the fifth respective magnetic grouping, and its second end magnet position is serially spaced and proximate to the first end magnet position of the second respective magnetic grouping.

21. A magnetic therapeutic, self-adjusting, penile band assembly for use in interaction with a penile organ of a human or animal, and in responsive interaction with physiologically, changing size and dimensions of a penile organ, said magnetic therapeutic, self-adjusting, penile band assembly comprising:

a penile band support subassembly having size-adjustment means for changing in dimensions and size to an initial perimeter size of a penile organ and to further and later changes in perimeter size of a penile organ, along a preselected installment site thereon, and means for retaining and positioning magnet components in adjacent positional relation along a perimeter of a penile organ; with which it interacts;

said penile band support subassembly being differentially layered, comprising a support layer having an arcuate perimeter and a preselected elastic, contractable and expandable, quality and construction, and a pocketing and spacing layer having an elastic, contractable and expandable, quality and construction greater than that of the support layer, the pocketing and spacing layer being dimensioned and attached to the support layer such that portions thereof are positionable in relation to the support layer, each of the layers being fabricated of construction materials, and fitted together, such that portions of each can bend and fold together at a plurality of locations spaced from one another; and a plurality of magnetic components, each having a positive end portion and a negative end portion, being positioned, supported, pocketed, and spaced from one another, between the support layer and the pocketing and spacing layer, each of the respective plurality of magnetic components being so positioned, supported, pocketed and spaced, in serial and positional relation to one another, along the arcuate perimeter of the support layer, such that each is distanced from one another and aligned in alternating, substantially positive and negative magnetic filed charge by virtue of the positioning of their respective positive and negative end portions.

22. The magnetic therapeutic, self-adjusting penile band assembly of claim 21, wherein each of the plurality of magnetic components comprises respective individual magnet members.

23. The magnetic therapeutic, self-adjusting penile band assembly of claim 21, wherein each of the plurality of magnetic components comprises multiple magnet members, each positioned in relation to one another so that their respective positive and negative end portions are proximate to one another, and together, respectively, cumulatively constitute, substantially, one magnetic charge therewithin.

24. A self-adjusting and differentially layered magnetic therapeutic penile system for use in contacted interaction with areas on a penile organ, while providing automatic dimensional adjustment, at a substantially uniform pressure, to dimensional and perimeter size changes of a living penile organ, said magnetic therapeutic penile system comprising:

a support band having first and second ends, inboard and outboard surface areas, and first and second perimeter portions;

a plurality of magnetic groupings, each having a number of individual magnet components, each of the individual magnet components having a South end, substantially South in magnetic field charge, a North end, substantially North in magnetic field charge, and a lateral-lengthwise portion separating the South and North ends, and being positioned serially and generally parallel in relation to one another on the inboard surface area of the support band, such that each of the magnetic groupings is spaced from each other, each of the individual magnet components of each magnetic grouping further being positionally aligned as to its South end and North end in relation to each of the first and second perimeter portions of the support band, so that along either such perimeter portion the South or North ends positionally aligned thereat are the same as to, and within, each individual magnetic grouping, and opposite in magnetic field charge as to each adjacently neighboring magnetic grouping, thereby positioning said magnetic groupings on the support band serially spaced from one another and of opposite magnetic field charge in neighboring relation to one another, and wherein each of the magnetic groupings is provided with at least two individual magnet components positioned together on the support band, generally at a middle position of each respective magnetic grouping and at least one individual magnet component positioned at a first end position on one adjacent side of the middle position and at a second end position on another adjacent side of the middle position, of each respective magnetic grouping on the support band, and wherein each of the first and second positions of each respective magnetic grouping is spaced from the middle position thereof;

a plurality of intra-magnet retainers, each being securely positioned about the individual magnet components positioned together at the middle position of each respective magnetic grouping on the support band;

said support band being differentially layered and further comprising a mesh layer having first and second ends and defining a plurality of open spaces, being positioned and secured over the magnetic groupings, in relation to the support band such that a separate securing pocket is created between the support band and said mesh layer as to each respective middle position and as to each of the first and second positions respectively adjacent thereto within each of the respective magnetic groupings, and such that each magnetic grouping is spaced from one another; and means for coupling the first end of the support band to the second end thereof.

* * * * *